(12) United States Patent
Liu et al.

(10) Patent No.: US 6,852,719 B2
(45) Date of Patent: Feb. 8, 2005

(54) GLUCOCORTICOID RECEPTOR MODULATORS

(75) Inventors: Kevin K. Liu, East Lyme, CT (US); Bradley P. Morgan, Lyme, CT (US); Ralph P. Robinson, Gales Ferry, CT (US)

(73) Assignees: Pfizer Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 10/012,274

(22) Filed: Oct. 26, 2001

(65) Prior Publication Data

US 2004/0014741 A1 Jan. 22, 2004

Related U.S. Application Data

(60) Provisional application No. 60/244,302, filed on Oct. 30, 2000.

(51) Int. Cl.[7] ............... A61K 31/4245; C07D 271/06
(52) U.S. Cl. ............ 514/236.2; 514/326; 514/340; 514/364; 544/138; 546/209; 546/269.1; 548/131
(58) Field of Search ............... 548/131; 546/209, 546/269.1; 544/138; 514/364, 236.2, 326, 340

(56) References Cited

U.S. PATENT DOCUMENTS

| | | | |
|---|---|---|---|
| 3,683,091 A | 8/1972 | Nagata et al. | 424/331 |
| 5,696,127 A | 12/1997 | Jones et al. | 514/285 |
| 5,767,113 A | 6/1998 | Cohn et al. | 514/176 |
| 6,380,223 B1 * | 4/2002 | Dow et al. | 514/357 |
| 6,699,893 B2 * | 3/2004 | Dow et al. | 514/357 |

FOREIGN PATENT DOCUMENTS

| | | | |
|---|---|---|---|
| EP | 0188396 | 7/1986 | ............... C07J/1/00 |
| EP | 0683172 | 8/1997 | ............ C07J/41/00 |
| EP | 0903146 | 3/1999 | .......... A61K/31/57 |
| JP | 4514056 | 5/1970 | |
| JP | 4536500 | 11/1970 | |
| JP | 50111098 | 9/1975 | ......... C07D/471/04 |
| JP | 6263688 | 9/1994 | ........... C07C/50/38 |
| JP | 9052899 | 2/1997 | ............. C07J/63/00 |
| WO | WO 9510266 | 4/1995 | .......... A61K/31/085 |
| WO | WO 9826783 | 6/1998 | .......... A61K/31/56 |
| WO | WO 9827986 | 7/1998 | .......... A61K/31/57 |
| WO | WO 9831702 | 7/1998 | ............ C07J/41/00 |
| WO | WO 9933786 | 7/1999 | ......... C07C/233/12 |
| WO | WO 9941256 | 8/1999 | ......... C07D/491/04 |
| WO | WO 9941257 | 8/1999 | ....... C07D/491/052 |
| WO | WO 9963976 | 12/1999 | .......... A61K/31/00 |
| WO | WO 0006137 | 2/2000 | .......... A61K/31/00 |
| WO | WO 0007972 | 2/2000 | ......... C07C/59/135 |
| WO | WO 0066522 | 11/2000 | ........... C07C/35/42 |
| ZA | 6706757 | 11/1967 | |

OTHER PUBLICATIONS

C.F. Bigge et al., J. Med. Chem., 1993, 36, 1977–1995, "Synthesis and Pharmacological Evaluation of 4a–Phenanthrenamine Derivatives Acting at the Phencyclidine Binding Site of the N–Methyl–D–aspartate Receptor Complex".

P. R. Kanjilal et al., J. Org. Chem., 1985, 50, 857–863, "Synthetic Studies toward Complex Diterpenoids. 16.[1] A Novel Synthetic Route to the Carbocyclic Skeleta of Stemodin and Stemarin by Acid–Catalyzed Intramolecular C–Alkylation and Rearrangement Reactions".

G. Sinha et al., J. Chem. Soc., Perkin Trans. I (1983), (10), 2519–2528, "Condensed Cyclic and Bridged–ring System. Part 9.[1] Stereocontrolled Synthesis and X–Ray Structural Analyses of cis–3,4,4a,9,10,10a–Hexahydro–1,4a–ethano-phenanthrene–2–(1H), 12–dione and trans–3,4,4a,9,10, 10a–Hexahydro–3,4–ethanophenanthrene–2(1H), 12–dione".

U. R. Ghatak et al., Tetrahedron Letters No. 32, pp. 2929–2932, 1978, "Angular Alkylation Through a Novel Intramolecular Cationic Reaction. A Simple Stereospecific Route to Polycyclic Bridged–Ring Intermediates Towards Some Complex Diterpenoids".

(List continued on next page.)

*Primary Examiner*—Laura L. Stockton
(74) *Attorney, Agent, or Firm*—Scully, Scott, Murphy & Presser

(57) ABSTRACT

The present invention provides non-steroidal compounds of Formula I, including prodrugs and pharmaceutically acceptable salts thereof, which are selective modulators (e.g., agonists, partial agonists and antagonists) of a steroid receptor, specifically, the glucocorticoid receptor. The present invention also provides pharmaceutical compositions containing these compounds and methods for using these compounds to treat animals requiring glucocorticoid receptor agonist or antagonist therapy. Glucocorticoid receptor modulators are useful to treat diseases, such as obesity, diabetes, inflammation and others as described below. The present invention also provides processes for preparing these compounds

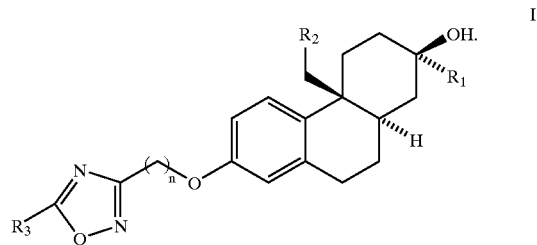

30 Claims, No Drawings

OTHER PUBLICATIONS

P. N. Chakrabortty et al., Indian J. Chem. (1974), 12(9), 948–55, "Synthetic Studies in Resin Acid Series: Part VII—Synthesis of 1α–Methyl–1β,4aβ–dicarboxy–1,2,3,4,4a,9,10,10aβ–octahydrophenanthrene & 1β,4aβ–Dicarboxy–1,2,3,4,4a,9,10,10aα–octahydrophenanthrene".

E. Fujita et al., J. Chem. Soc., Perkin Trans. I (1974), (1), 165–77, "Terpenoids. Part XXVIII.[1] Total Synthesis of Enmein[2]".

H. Sdassi et al., Synthetic Communications, 25(17), 2569–2573 (1995), "Enantioselective Synthesis of (R)–(+)–4a–Cyanomethyl–6–Methoxy–3,4,9,10–Tetrahydrophenanthren–2–one".

T. Ibuka et al., Yakugaku Zasshi (1967), 87(8), 1014–17, "Studies on the Alkaloids of Menispermaceous Plants. CCXXXVI.[3]"(and English language translation).

D. Bonnet–Delpon et al., Tetrahedron (1996), 52(1), 59–70, "Trifluoromethylalkenes in Cycloaddition Reactions#".

J. A. Findlay et al., Tetrahedron Letters No. 19, pp. 869–872, 1962, "Synthesis in the Diterpene Alkaloid Series—I—The Stereospecific Synthesis of an Intermediate and its Identification With a Natural Degradation Product".

* cited by examiner

GLUCOCORTICOID RECEPTOR MODULATORS

CROSS REFERENCE TO RELATED APPLICATION

This application claims the benefit of U.S. Provisional Application No. 60/244,302 filed Oct. 30, 2000.

FIELD OF THE INVENTION

The present invention provides non-steroidal compounds which are selective modulators (e.g., agonists, partial agonists and/or antagonists) of a steroid receptor, specifically, the glucocorticoid receptor. The present invention also provides pharmaceutical compositions containing these compounds and methods for using these compounds to treat animals requiring glucocorticoid receptor agonist and/or antagonist therapy. Glucocorticoid receptor modulators are useful to treat diseases such as obesity, diabetes, inflammation and others as described below. The present invention also provides processes for preparing these compounds.

BACKGROUND OF THE INVENTION

Nuclear receptors are classically defined as a family of ligand dependent transcription factors that are activated in response to ligand binding (R. M. Evans, 240 Science, 889 (1988)). Members of this family include the following receptors: glucocorticoid, mineralocorticoid, androgen, progesterone and estrogen. Naturally occurring ligands to these receptors are low molecular weight molecules that play an important role in health and in many diseases. Excesses or deficiencies of these ligands can have profound physiological consequences. As an example, glucocorticoid excess results in Cushing's Syndrome, while glucocorticoid insufficiency results in Addison's Disease.

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist.

U.S. Pat. No. 3,683,091 discloses phenanthrene compounds, specifically certain di-7-hydroxy or methyl-2, 3,4,4a,9,10-hexahydrophenanthren-2-one and 4a-alkyl derivatives, hydrogenated derivatives, functional derivatives and optically active isomers thereof useful as specific anti-acne agents.

Japanese Patent Application, Publication No. 45014056, published 20 May 1970, discloses the manufacture of 1,2, 3,4,9,10,11α,12-octahydro-7-methoxy-12β-butylphenanthren-2β-ol and certain of its derivatives useful as antiandrogenic and antianabolic drugs.

Japanese Patent Application, Publication No. 6-263688, published 20 Sep. 1994, discloses certain phenanthrene derivatives which are interleukin-1 (IL-1) inhibitors. It also discloses their preparation and certain intermediates thereto. International Patent Application Publication No. WO 95/10266, published 20 Apr. 1995, discloses the preparation and formulation of certain phenanthrene derivatives as nitrogen monoxide synthesis inhibitors.

Japanese Patent Application, Publication No. 45-36500, published 20 Nov. 1970, discloses a method of making certain optically active phenanthrene derivatives which are useful as antiandrogenic agents.

European Patent Application, Publication No. 0 188 396, published 23 Jul. 1986, discloses certain substituted steroid compounds, certain process and intermediates for preparing them, their use and pharmaceutical compositions containing them. These compounds are disclosed to possess antiglucocorticoid activity, and some of them have glucocorticoid activity.

C. F. Bigge et al., J. Med. Chem. 1993, 36, 1977–1995, discloses the synthesis and pharmacolgical evaluation of a series of octahydrophenanthrenamines and certain of their heterocyclic analogues as potential noncompetitive antagonists of the N-methyl-D-aspartate receptor complex.

P. R. Kanjilal et al., J. Org. Chem. 1985, 50, 857–863, discloses synthetic studies toward the preparation of certain complex diterpenoids.

G. Sinha et al., J. Chem. Soc., Perkin Trans. I (1983), (10), 2519–2528, discloses the synthesis of the isomeric bridged diketones cis-3,4,4a,9,10,10a-hexahydro-1,4a-ethanophenanthren-2(1H),12-dione and trans-3,4,4a,9,10, 10a-hexahydro-3,4a-ethanophenanthren-2(1H),12-dione by highly regioselective intramolecular aldol condensations through the stereochemically defined cis- and trans-2,2-ethylenedioxy-1,2,3,4,4a,9,10,10a-octahydrophenanthren-4a-ylacetaldehydes.

U. R. Ghatak, M. Sarkar and S. K. Patra, Tetrahedron Letters No. 32, pp. 2929–2931, 1978, discloses a simple stereospecific route to certain polycyclic bridged-ring intermediates useful in preparing some complex diterpenoids.

P. N. Chakrabortty et al., Indian J. Chem. (1974), 12(9), 948–55, discloses the synthesis of 1α-methyl-1β,4aβ-dicarboxy-1,2,3,4,4a,9,10,10aβ-octahydro-phenanthrene, an intermediate in the synthesis of certain diterpenoids and diterpene alkaloids, and of 1β,4aβ-dicarboxy-1,2,3,4,4a,9, 10,10aα-octahydrophenanthrene.

E. Fujita et al., J. Chem. Soc., Perkin Trans. I (1974), (1), 165–77, discloses the preparation of enmein from 5-methoxy-2-tetralone via ent-3-β,2-epoxy-3-methoxy-17-norkaurane-6α, 16α-diol.

H. Sdassi et al., Synthetic Communications, 25(17), 2569–2573 (1995) discloses the enantioselective synthesis of (R)-(+)-4a-cyanomethyl-6-methoxy-3,4,9,10-tetrahydrophenanthren-2-one, which is a key intermediate in morphinan synthesis.

T. Ibuka et al., Yakugaku Zasshi (1967), 87(8), 1014–17, discloses certain alkaloids of menispermaceous plants.

Japanese Patent 09052899, dated 25 Feb. 1997, discloses certain diterpene or triterpene derivatives which are leukotriene antagonists obtained by extraction from *Tripterygium wilfordii* for therapeutic use.

U.S. Pat. No. 5,696,127 discloses certain nonsteroidal compounds, such as 5H-chromeno[3,4-f]quinolines, which are selective modulators of steroid receptors.

U.S. Pat. No. 5,767,113 discloses certain synthetic steroid compounds useful for concurrently activating glucocorticoid-induced response and reducing multidrug resistance.

Published European Patent Application 0 683 172, published 11 Nov. 1995, discloses certain 11,21-bisphenyl-19-norpregnane derivatives having anti-glucocorticoid activity and which can be used to treat or prevent glucocorticoid-dependent diseases.

D. Bonnet-Delpon et al., Tetrahedron (1996), 52(1), 59–70, discloses certain $CF_3$-substituted alkenes as good partners in Diels-Alder reactions with Danishefsky's diene and in 1,3-dipolar cycloadditions with certain nitrones and non-stabilized azomethine ylides.

International Patent Application Publication No. WO 98/26783, published 25 Jun. 1998, discloses the use of certain steroid compounds with anti-glucocorticoid activity, with the exception of mifepristone, for preparing medicaments for the prevention or treatment of psychoses or addictive behavior.

International Patent Application Publication No. WO 98/27986, published 2 Jul. 1998, discloses methods for treating non-insulin dependent Diabetes Mellitus (NIDDM), or Type II Diabetes, by administering a combination of treatment agents exhibiting glucocorticoid receptor type I agonist activity and glucocorticoid receptor type II antagonist activity. Treatment agents such as certain steroid compounds having both glucocorticoid receptor type I agonist activity and glucocorticoid receptor type II antagonist activity are also disclosed.

International Patent Application Publication No. WO 98/31702, published 23 Jul. 1998, discloses certain 16-hydroxy-11-(substituted phenyl)-estra-4,9-diene derivatives useful in the treatment or prophylaxis of glucocorticoid dependent diseases or symptoms.

Published European Patent Application 0 903 146, published 24 Mar. 1999, discloses that the steroid 21-hydroxy-6,19-oxidoprogesterone (21OH-6OP) has been found to be a selective antiglucocorticoid and is used for the treatment of diseases associated with an excess of glucocorticoids in the body, such as Cushing's syndrome or depression.

J. A. Findlay et al, Tetrahedron Letters No. 19, pp. 869–872, 1962, discloses certain intermediates in the synthesis of diterpene alkaloids.

Published German Patent Application DE 19856475, published 31 May 2000, discloses the preparation of certain N-heterocyclyl-α-hydroxyalkanamides and analogs as glucocorticoid receptor ligands.

International Patent Application Publication Nos. WO 99/41256 and WO 99/41257, published 19 Aug. 1999, disclose certain benzopyrano[3,4-f]quinoline derivatives as glucocorticoid receptor modulators, useful for the treatment of, e.g., inflammation, immune and autoimmune diseases.

International Patent Application Publication No. WO 00/06137, published 10 Feb. 2000, discloses certain 4-aminotriphenylmethane derivatives which are selective glucocorticoid receptor ligands.

International Patent Application Publication No. WO 99/33786, published 8 Jul. 1999, discloses certain triphenylpropylamine and triphenylcyclopropylamine derivatives as anti-inflammatory compounds.

International Patent Application Publication No. WO 99/63976, published 16 Dec. 1999, discloses the use of a specific liver-selective glucocorticoid antagonist, {3,5-dibromo-4-[5-isopropyl-4-methoxy-2-(3-methyl-benzoyl)-phenoxy]phenyl}-acetic acid, for the preparation of a pharmaceutical composition for the treatment of diabetes.

International Patent Application Publication No. WO 00/07972, published 17 Feb. 2000, discloses certain glucocorticoid and thyroid receptor ligands which are useful for the treatment and prevention of diseases associated with metabolism dysfunction, e.g., diabetes.

Glucocorticoid receptor modulators are disclosed in International patent application PCT/IB00/00366, filed 27 Mar. 2000, and assigned to the assignee hereof.

Although there are glucocorticoid receptor therapies in the art, there is a continuing need for and a continuing search in this field of art for selective glucocorticoid receptor therapies. Thus, the identification of non-steroidal compounds which have specificity for one or more steroid receptors, but which have reduced or no cross-reactivity for other steroid or intracellular receptors, is of significant value in this field.

SUMMARY OF THE INVENTION

The present invention provides compounds of Formula I

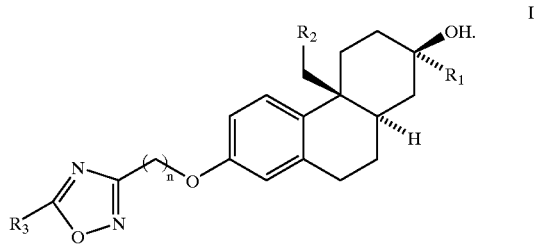

prodrugs of said compounds or pharmaceutically acceptable salts of said compounds or prodrugs;

wherein $R_1$ is a) —($C_1$–$C_6$)alkyl optionally substituted with —$CF_3$, b) —C≡C—$CH_3$, c) —C≡C—Cl, d) —C≡C—$CF_3$, e) —$CH_2O$($C_1$–$C_4$)alkyl optionally substituted with —$CF_3$ or f) —$CF_3$;

$R_2$ is a) —($C_1$–$C_5$)alkyl, b) —($C_2$–$C_5$)alkenyl or c)-phenyl optionally substituted with one of the following: —OH, —$NR_8R_9$, —$NR_8$—C(O)—($C_1$–$C_4$) alkyl, —CN, —Z-het, —O—($C_1$–$C_3$)alkyl-C(O)—$NR_8R_9$, —$NR_8$—Z—C(O)—$NR_8R_9$, —Z—$NR_8$—$SO_2$—$R_9$, —$NR_8$—$SO_2$-het, —O—C(O)—($C_1$–$C_4$) alkyl or —O—$SO_2$—($C_1$–$C_4$)alkyl;

Z for each occurrence is independently —($C_0$–$C_4$)alkyl;

$R_3$ is a) —($C_1$–$C_6$)alkyl, b) —Z—$NR_4R_5$ or c) —Z-het;

$R_4$ and $R_5$ are each independently a) hydrogen or b) —($C_1$–$C_3$)alkyl;

het is an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring; and optionally substituted with one to three $R_6$;

$R_6$ is a) —($C_1$–$C_6$)alkyl optionally substituted with one to three $R_7$, b) —Z—$NR_8R_9$ or c) —Z—C(O)—$NR_8R_9$;

$R_7$ for each occurrence is independently a) halo, b) —OH, c) oxo or d) —O($C_1$–$C_6$)alkyl;

$R_8$ and $R_9$ for each occurrence are independently a) —H or b) —($C_1$–$C_3$)alkyl;

or $R_8$ and $R_9$ are taken together with N to form het;
n is one to three;
provided that:
1) when $R_1$ is —C≡C—$CH_3$, $R_2$ is phenyl and n is one, then $R_3$ is other than —$CH_2$—N($CH_3$)$_2$, —($CH_2$)$_2$—N($CH_3$)$_2$, —$CH_2$-piperidinyl or —($CH_2$)$_2$-morpholiny;
2) when $R_1$ is —($CH_2$)$_2$—$CH_3$, $R_2$ is phenyl and n is one, then $R_3$ is other than -t-butyl or -3,5-dimethyl-4-isoxazolyl.

More particularly, the present invention provides compounds of Formula II

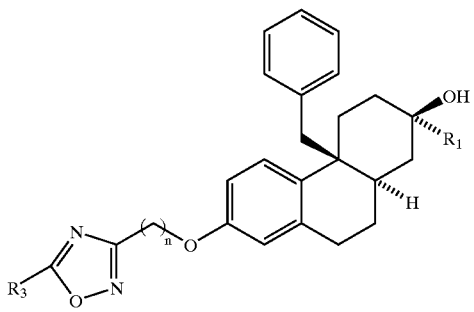

II a prodrug of said compound or a pharmaceutically acceptable salt of said compound or prodrug; wherein $R_1$ is a) —($C_1$-$C_6$)alkyl optionally substituted with —$CF_3$, b) —C≡C—$CH_3$, c) —$CF_3$ or d) —$CH_2O(C_2$-$C_4)$alkyl; and n is one or two.

More particularly, the present invention provides such compounds wherein $R_1$ is a) —$CH_2CH_2CH_3$, b) —C≡C—$CH_3$ or c) —$CF_3$; and n is one. More particularly, the present invention provides such compounds wherein $R_1$ is a) —$CH_2CH_2CH_3$ or b) $CF_3$.

More particularly, the present invention provides such compounds wherein $R_3$ is —($C_1$-$C_2$)alkyl-$NR_4R_5$; and $R_4$ and $R_5$ are each independently a) methyl, b) ethyl, c) propyl or d) isopropyl. Even more particularly, the present invention provides such compounds wherein $R_3$ is —($C_1$-$C_2$)alkyl-$NR_4R_5$; and $R_4$ and $R_5$ are each independently a) methyl or b) ethyl.

More particularly, the present invention provides such compounds wherein $R_3$ is —($C_0$-$C_2$)alkyl-het; het is a) morpholinyl, b) pyrrolidinyl, c) piperidinyl, d) piperazinyl, e) hexahydro-azepinyl, f) azabicyclo[2.2.2]oct-3-yl, g) azabicyclo[3.2.1]oct-3-yl, h) 3,6-diazabicyclo[3.1.1]heptyl, i) 2,5-diazabicyclo[2.2.1]heptyl, j) 1,2,5,6-tetrahydro-pyridinyl, k) azetidinyl, l) 1,4-diazabicyclo[3.2.2]nonanyl, m) 3,6-diazabicyclo[3.2.2]nonanyl, n) octahydro-pyrido[1,2-a]pyrazinyl or o) hexahydro-1,4-diazepinyl; the above het groups are optionally substituted with one or two $R_6$; $R_6$ for each occurrence is independently a) methyl, b) ethyl or c) —$NR_8R_9$; and $R_8$ and $R_9$ for each occurrence are independently methyl or ethyl. Even more particularly, the present invention provides such compounds wherein $R_3$ is —($C_0$-$C_2$)alkyl-het; het is a) morpholinyl, b) piperidinyl, c) 1,2,5,6-tetrahydro-pyridinyl, d) azetidinyl or e) pyrrolidinyl; the above het groups are optionally substituted with one or two $R_6$; $R_6$ for each occurrence is independently a) methyl or b) ethyl.

The present invention also provides compounds of Formula I wherein $R_1$ is a) —$CH_2CH_2CH_3$, b) —C≡C—$CH_3$ or c) —$CF_3$; $R_2$ is a) methyl, b) ethyl, c) propyl, d) ethenyl or e) propenyl; $R_3$ is —($C_1$-$C_2$)alkyl-$NR_4R_5$; $R_4$ and $R_5$ are each independently a) methyl or b) ethyl; and n is one.

The present invention also provides compounds of Formula I wherein $R_1$ is a) —$CH_2CH_2CH_3$, b) —C≡C—$CH_3$ or c) —$CF_3$; $R_2$ is a) methyl, b) ethyl, c) propyl, d) ethenyl or e) propenyl; $R_3$ is —($C_0$-$C_2$)alkyl-het; het is a) morpholinyl, b) piperidinyl or c) pyrrolidinyl; the above het groups are optionally substituted with one or two $R_6$; $R_6$ for each occurrence is independently a) methyl or b) ethyl; and n is one.

The present invention also provides methods for the treatment of a glucocorticoid receptor-mediated disease or condition in a mammal, which comprises administering to the mammal a therapeutically effective amount of a compound of claim 1, a prodrug of said compound or a pharmaceutically acceptable salt of said compound or prodrug. More particularly, the present invention provides such methods wherein the glucocorticoid receptor-mediated disease or condition is selected from the group consisting of obesity, diabetes, depression, anxiety and neurodegeneration. Even more particularly, the present invention provides such methods wherein the condition is obesity. Even more particularly, the present invention provides such methods, which further comprise administering a $\beta_3$ agonist, a thyromimetic agent, an eating behavior modifying agent or a NPY antagonist. Even more particularly, the present invention provides such methods wherein the eating behavior modifying agent is orlistat or sibutramine. Also, the present invention provides such methods wherein the disease is diabetes. Even more particularly, the present invention provides such methods which further comprise administering an aldose reductase inhibitor, a glycogen phosphorylase inhibitor, a sorbitol dehydrogenase inhibitor, insulin, a sulfonylurea, glipizide, glyburide, or chlorpropamide. Also, the present invention provides such methods wherein the glucocorticoid receptor-mediated disease is an inflammatory disease.

The present invention also provides pharmaceutical compositions comprising a therapeutically effective amount of a compound of claim 1, a prodrug of said compound or a pharmaceutically acceptable salt of said compound or prodrug; and a pharmaceutically acceptable carrier, vehicle or diluent.

The present invention also provides pharmaceutical combination compositions comprising: a therapeutically effective amount of a composition comprising:
  a first compound, said first compound being a compound of claim 1, a prodrug of said compound or a pharmaceutically acceptable salt of said compound or prodrug; and
  a second compound, said second compound being a $\beta_3$ agonist, a thyromimetic agent, an eating behavior modifying agent or a NPY antagonist.

The present invention also provides kits comprising:
a) a first compound, said first compound being a compound of claim 1, a prodrug of said compound or a pharmaceutically acceptable salt of said compound or prodrug and a pharmaceutically acceptable carrier, vehicle or diluent in a first unit dosage form;
b) a second compound, said second compound being a $\beta_3$ agonist, a thyromimetic agent, an eating behavior modifying agent or a NPY antagonist; and a pharmaceutically acceptable carrier, vehicle or diluent in a second unit dosage form; and
c) a container for containing said first and second dosage forms; wherein the amounts of said first and second compounds result in a therapeutic effect.

The present invention also provides methods for inducing weight loss in a mammal which comprises administering to the mammal a therapeutically effective amount of a compound of claim 1, a prodrug of said compound a pharmaceutically acceptable salt of said compound or prodrug.

The present invention also provides pharmaceutical combination compositions comprising: a therapeutically effective amount of a composition comprising:
- a first compound, said first compound being a compound of claim 1, a prodrug of said compound or a pharmaceutically acceptable salt of said compound or prodrug; and
- a second compound, said second compound being an aldose reductase inhibitor, a glycogen phosphorylase inhibitor, a sorbitol dehydrogenase inhibitor, insulin, a sulfonylureas, glipizide, glyburide, or chlorpropamide.

The present invention also provides methods for the treatment of an inflammatory disease in a mammal which comprises administering to said mammal a therapeutically effective amount of a compound of claim 1, a prodrug of said compound or a pharmaceutically acceptable salt of said compound or prodrug. Even more particularly, the present invention provides such methods wherein the inflammatory disease is selected from the group consisting of arthritis, asthma, rhinitis and immunomodulation.

Also, the present invention provides processes for preparing a compound of Formula II

II

[Structure of Formula II]

wherein $R_1$ is a) —$(C_1$-$C_3)$alkyl, b) —C≡C—$CH_3$, c) —$CF_3$ or d) —$CH_2O(C_2$-$C_4)$alkyl;

Z for each occurrence is independently —$(C_0$-$C_4)$alkyl;

$R_3$ is a) —$(C_1$-$C_6)$alkyl, b) —Z—$NR_4R_5$ or c) —Z-het;

$R_4$ and $R_5$ are each independently a) hydrogen or b) —$(C_1$-$C_3)$alkyl;

het is an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring; and optionally substituted with one to three $R_6$;

$R_6$ is a) —$(C_1$-$C_6)$alkyl optionally substituted with one to three $R_7$, b) —Z—$NR_8R_9$ or c) —Z—C(O)—$NR_8R_9$;

$R_7$ for each occurrence is independently a) halo, b) —OH, c) oxo or d) —O$(C_1$-$C_6)$alkyl;

$R_8$ and $R_9$ are for each occurrence independently a) —H or b) —$(C_1$-$C_3)$alkyl;

or $R_8$ and $R_9$ are taken together with N to form het;

n is one to three;

which comprises a) reacting a compound of formula II-A

II-A

[Structure of Formula II-A]

wherein $R_1$ is as defined above, with V—$(CH_2)_n$—CN, wherein V is a halogen or a leaving group and n is one to three, and a base in an aprotic solvent to give a compound of formula II-B

II-B

[Structure of Formula II-B]

b) reacting the compound of formula II-B with hydroxyamine or its HCl salt in a protic solvent and a base to give the compound of formula II-C

II-C

[Structure of Formula II-C]

c) reacting the compound of formula II-C with an acetylating agent and a base in an aprotic solvent to give the final compound of formula II.

More particularly, the present invention provides such processes wherein in step a) the leaving group is tosylate or mesylate, the base is $Et_3N$ and the aprotic solvent is THF or $CH_3CN$. More particularly, the present invention provides such processes wherein in step b) the protic solvent is ethanol or methanol and the base is $K_2CO_3$. More particularly, the present invention provides such processes wherein in step c) the acetylating agent is carboxylic acid chloride, anhydride or alkyl ester, the base is pyridine and the aprotic solvent is DMF.

Also, the present invention provides compounds of formula II-B

II-B

[Structure of Formula II-B]

wherein n is one to three; and
$R_1$ is a) —$(C_1$-$C_3)$alkyl, b) —C≡C—$CH_3$, c) —$CF_3$ or d) —$CH_2O(C_2$-$C_4)$alkyl.

Finally, the present invention provides compounds of formula II-C

II-C

[Structure of Formula II-C]

wherein n is one to three; and
$R_1$ is a) —$(C_1$-$C_3)$alkyl, b) —C≡C—$CH_3$, c) —$CF_3$ or d) —$CH_2O$ $(C_2$-$C_4)$alkyl.

DETAILED DESCRIPTION OF THE INVENTION

The compounds of the present invention are named according to the IUPAC or CAS nomenclature system.

In one way of naming the compounds of the present invention, the carbon atoms in the ring may be numbered as shown in the following simplified structure:

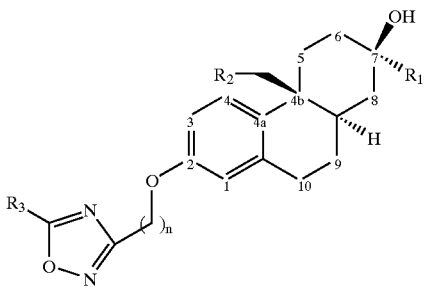

Alternatively, another way of naming the compounds of the present invention, the carbon atoms in the ring may be numbered as shown in the following simplified structure:

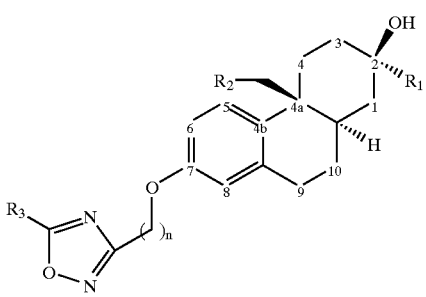

The carbon atom content of various hydrocarbon-containing moieties is indicated by a prefix designating the minimum and maximum number of carbon atoms in the moiety, i.e., the prefix $C_i$–$C_j$ indicates a moiety of the integer "i" to the integer "j" carbon atoms, inclusive. Thus, for example, $C_1$–$C_3$ alkyl refers to alkyl of one to three carbon atoms, inclusive, or methyl, ethyl, propyl and isopropyl, and all isomeric forms and straight and branched forms thereof.

Examples of alkyl of one to six carbon atoms, inclusive, are methyl, ethyl, propyl, butyl, pentyl and hexyl, and all isomeric forms and straight and branched thereof.

Examples of alkenyl of two to five carbon atoms, inclusive, are ethenyl, propenyl, butenyl, pentenyl and hexenyl, and all isomeric forms and straight and branched forms thereof.

Examples of alkynyl of two to six carbon atoms, inclusive, are ethynyl, propynyl, butynyl, pentynyl and hexynyl, and all isomeric forms and straight and branched forms thereof.

The terms cycloalkyl, cycloalkenyl and cycloalkynyl refer to cyclic forms of alkyl, alkenyl and alkynyl, respectively. Exemplary ($C_3$–$C_8$)cycloalkyl groups are cyclopropyl, cyclobutyl, cyclopentyl, cyclohexyl, cycloheptyl and cyclooctyl.

The term halo includes chloro, bromo, iodo and fluoro.

The term aryl refers to an optionally substituted six-membered aromatic ring, including polyaromatic rings. Examples of aryl include phenyl, naphthyl and biphenyl.

The term het refers to an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring. The heterocyclic ring, including each heteroatom, can be unsubstituted or substituted with one to three independent substituents, as chemically feasible.

The following paragraphs describe exemplary ring(s) for the generic ring descriptions contained herein.

Exemplary five-membered rings are furyl, thienyl, 2H-pyrrolyl, 3H-pyrrolyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 1,2,3,4-oxatriazolyl, 1,2,3,5-oxatrizaolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Exemplary six-membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-trizainyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl, 1,3,5,2-oxadiazinyl, azabicyclo[2.2.2]oct-3-yl (or quinuclidinyl) and azabicyclo [3.2.1]oct-3-yl (or tropanyl).

Exemplary seven-membered rings are azepinyl, oxepinyl, thiepinyl and 1,2,4-diazepinyl.

Exemplary eight membered rings are azacyclooctyl, azacyclooctenyl, azacyclooctadienyl, oxacyclooctyl, oxacyclooctenyl, oxacyclooctadienyl, thiocyclooctyl, thiocyclooctenyl and thiocyclooctadienyl.

Exemplary bicyclic rings consisting of combinations of two fused partially saturated, fully saturated or fully unsaturated five or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

As used herein the term "mammals" is meant to refer to all mammals, including, for example, primates such as humans and monkeys. Examples of other mammals included herein are rabbits, dogs, cats, cattle, goats, sheep and horses. Preferably, the mammal is a female or male human.

The term "treating", "treat" or "treatment" as used herein includes preventative (e.g., prophylactic) and palliative treatment.

The term "therapeutically effective amount" means an amount of a compound of the present invention that ameliorates, attenuates or eliminates a particular disease or condition or prevents or delays the onset of a particular disease or condition.

The phrase "compound(s) of the present invention" or "compound(s) of Formula I" or the like, shall at all times be understood to include all active forms of such compounds, including, for example, the free form thereof, e.g., the free acid or base form, and also, all prodrugs, polymorphs, hydrates, solvates, tautomers, and the like, and all pharmaceutically acceptable salts, unless specifically stated otherwise. It will also be appreciated that suitable active metabolites of such compounds are within the scope of the present invention.

By "pharmaceutically acceptable" it is meant the carrier, vehicle, diluent, excipient and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free phenol, and such hydrolyzable ester-forming residues of the Formula I compounds include, but are not limited to, those having a carboxyl moiety wherein the free hydrogen is replaced by $(C_1-C_4)$alkyl, $(C_2-C_7)$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

The compounds of Formula I of the present invention are prepared as described in the Schemes, Preparations and Examples below, or are prepared by methods analogous thereto, which are readily known and available to one of ordinary skill in light of this disclosure. In each of the Schemes, the R groups (e.g., $R_1$, $R_2$, etc.) correspond to those noted in the Summary above. However, it will be understood by those skilled in the art that other functionalities disclosed herein at the indicated positions of compounds of Formula I also comprise potential substituents for the analogous positions on the structures within the Schemes.

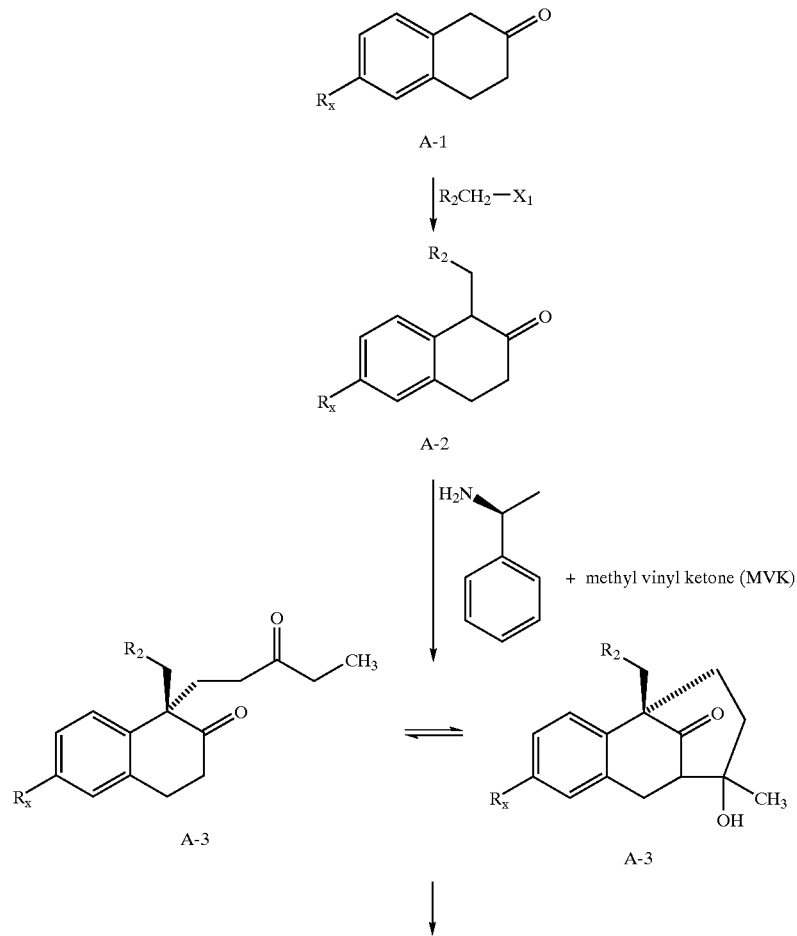

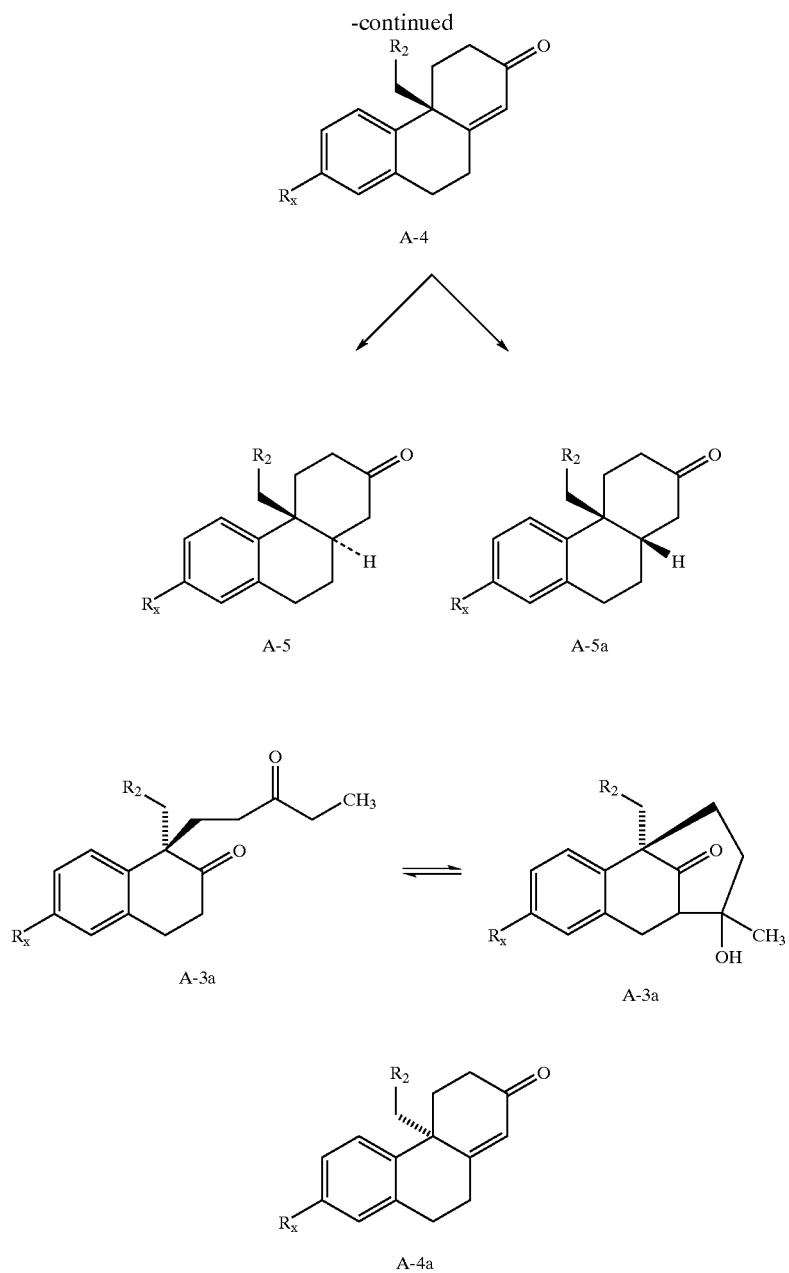

Scheme A

The compound of formula A-1 (prepared as described in Org. Syn. 1971, 51, 109–112) ($R_x$ is halogen or methyl ether) is reacted with a nitrogen-containing base, such as pyrrolidine, piperidine or morpholine, at a refluxing temperature in an aprotic solvent such as toluene, benzene, dichloromethane or dioxane. It is then reacted with the appropriate alkylating agent of formula $R_2CH_2$—$X_1$ wherein $R_2$ is ($C_1$–$C_5$)alkyl straight chain, isopropyl, t-butyl, phenyl or is as described in the Summary above, and $X_1$ is a leaving group (see, e.g., Francis A. Carey, in *Advanced Organic Chemistry*, $2^{nd}$ ed., Part A, Chapter 5.6, 1984) in toluene, dioxane, methanol, ethanol, isopropanol, DMF, DMSO or THF to give the compound of formula A-2. Typical alkylating agents are primary, secondary, benzylic or allylic halides and are preferably alkyl bromides or alkyl iodides.

Alternatively, the compound of formula A-1 is converted to its anion with a strong base, such as sodium hydride, sodium methoxide, lithium diisopropylamide, lithium bis(trimethylsilyl)amide, potassium bis(trimethylsilyl)amide, potassium t-butoxide or others, in an aprotic solvent, such as dimethylformamide (DMF) or tetrahydrofuran (THF). This reaction is conducted at −78° C. to room temperature depending on the nature of the base used. The resulting anion is alkylated with the appropriate alkylating agent of formula $R_2CH_2$—$X_1$ as defined above to give the compound of formula A-2.

Alternatively, the compound of formula A-1 is reacted with $R_2CH_2$—CHO and a base such as pyrrolidine or an acid such as acetic acid or hydrochloric acid in a solvent such as toluene, benzene, methanol or ethanol. The intermediate thus obtained is then hydrogenated using a palladium on carbon catalyst or numerous other reagents such as platinum oxide or rhodium on aluminum oxide (see P. N. Rylander in *Hydrogenation Methods*, Academic Press, New York, 1985; Herbert O. House in *Modern Synthetic Reactions*, $2^{nd}$ ed., Chapter 1, pp. 1–45, 1972; and John Fried and John A. Edwards in *Organic Reactions in Steroid Chemistry*, Chapter 3, pp. 111–145, 1972) to give the compound of formula A-2. Alternatively, the intermediate is reacted with a reducing metal reagent, such as an alkali (group IA in the periodic table) or alkaline metal (group IIA in the periodic table), including Li, Na, or Ca, and an amine, such as $NH_3$ or ethylene diamine, in an aprotic solvent, such as THF or dioxane, at −78° C. to room temperature to give the compound of formula A-2.

The compound of formula A-2 is reacted with (S)-(−)-α-methylbenzylamine (as shown in Scheme A) and an electrophile such as methyl vinyl ketone (MVK), as shown in Scheme A. The resulting major intermediate of formula A-3 may be ring closed or ring opened as illustrated in Scheme A.

Alternatively, the compound of formula A-2 is reacted with an electrophile such as MVK and a base such as sodium methoxide or potassium hydroxide or a racemic amine such as methylbenzylamine, piperidine, morphine or pyrrolidine in a solvent such as methanol to give a racemic mixture of the intermediates of formula A-3 and A-3a (as shown at the bottom of Scheme A). This reaction may also give directly a racemic mixture of the products A-4 and A-4a (as shown at the bottom of Scheme A), which mixtures may be resolved by chiral HPLC or by other literature methods for separating racemates.

The intermediate of formula A-3 is reacted with a base such as sodium methoxide or KOH in a solvent such as methanol or is reacted with an acid such as p-toluenesulfonic acid in a solvent such as toluene to give the compound of formula A-4, wherein $R_2$ is defined in the Summary above and wherein $R_x$ is halogen or methyl ether.

Alternatively, the compound of formula A-4 is prepared from the compound of formula A-3, by other reported annulation methods, some of which are described in M. E. Jung, *Tetrahedron*, 1976, 32, pp. 3–31.

The compound of formula A-4 wherein $R_x$ is, for example, methoxy is reacted with $BBr_3$ or $BCl_3$ and tetrabutylammonium iodide or dimethylboron bromide in an aprotic solvent such as dichloromethane or toluene at −78° C. to room temperature to give the compound of formula A-4 wherein $R_x$ is, for example, hydroxy.

Alternatively, the compound of formula A-4 wherein $R_x$ is, for example, methoxy is reacted with sodium ethanethiol in DMF or is reacted with methionine in methanesulfonic acid to give the compound of formula A-4 wherein $R_x$ is, for example, hydroxy.

Also, the compound of formula A-4 wherein $R_x$ is, for example, hydroxy may be prepared by other literature methods as described in *Protecting Groups in Organic Synthesis*, Third Edition, T. W. Greene and P. G. M. Wuts, John Wiley and Sons, Inc. (1999) or as illustrated in *Comprehesive Organic Transformation*, R. C. Larock, VCH Publishers Inc. (1989), pp. 501–527.

The compound of formula A-4 wherein $R_5$ is methyl ether or hydroxy is reacted with a reducing metal reagent, such as an alkali (group IA in the periodic table) or alkaline metal (group IIA in the periodic table), including Li, Na, or Ca, and an amine such as $NH_3$ or ethylene diamine in an aprotic solvent such as THF or dioxane at −78° C. to room temperature to give the compounds of formula A-5 and A-5a wherein $R_2$ is defined in the Summary above and wherein the trans-compound of formula A-5 is the major product.

SCHEME B

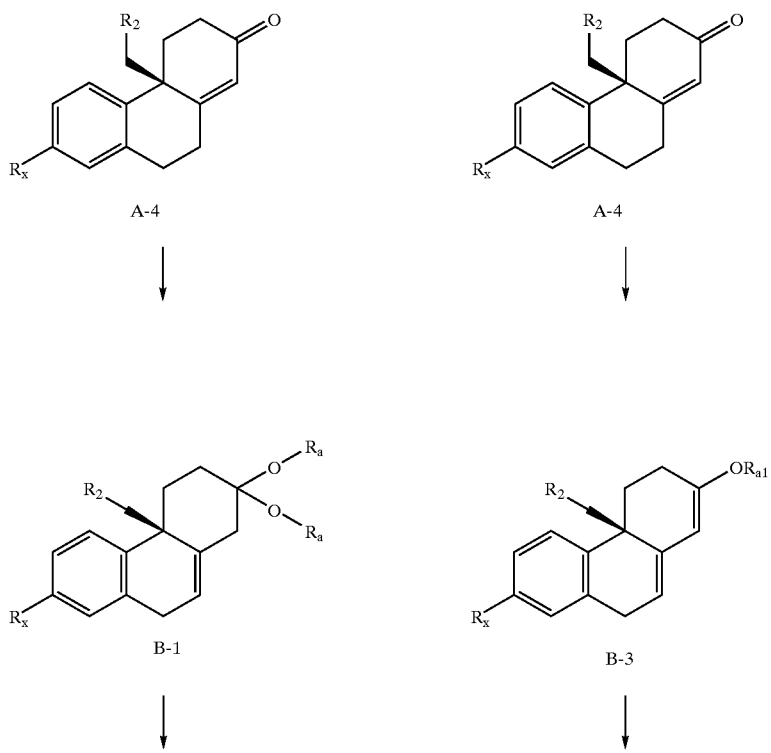

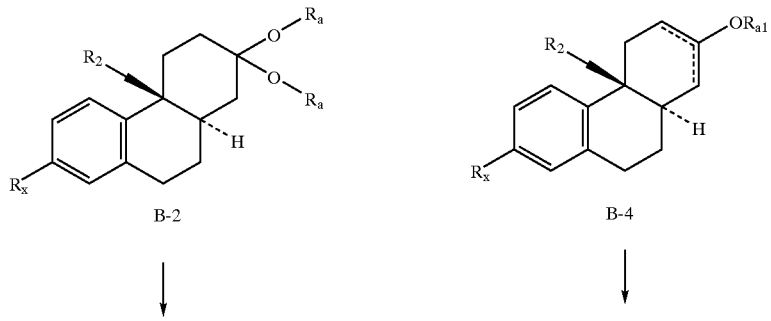

B-2     B-4

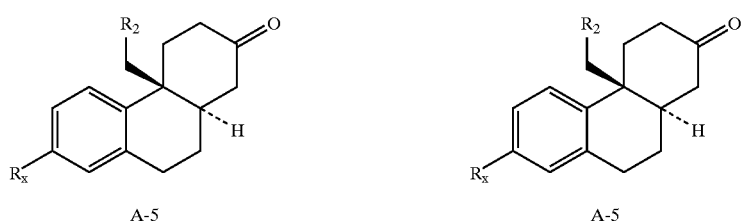

A-5     A-5

Scheme B

Alternatively, as shown in Scheme B, for example, the compound of formula A-4 from Scheme A wherein $R_x$ is halogen, methyl ether or hydroxy and $R_2$ is defined in the Summary above is treated with an alcohol or diol such as methanol, ethanol or ethylene glycol and a strong acid such as p-toluenesulfonic acid or HCl in an aprotic solvent such as toluene or benzene to form a ketal intermediate of formula B-1 wherein $R_a$ is lower alkyl or wherein the $R_a$'s taken together with the two oxygen atoms form, for example, 1,3-dioxolane and wherein $R_2$ is defined in the Summary above. Alternatively, this ketal intermediate may be prepared by other literature methods such as those described in *Protecting Groups in Organic Synthesis*, Third Edition, T. W. Greene and P. G. M. Wuts, John Wiley and Sons, Inc. (1999).

The ketal intermediate B-1 is hydrogenated using $Pd(OH)_2$ on carbon or other reagents, such as platinum oxide or rhodium on aluminum oxide (see P. N. Rylander in *Hydrogenation Methods*, Academic Press, New York, 1985; Herbert O. House in *Modern Synthetic Reactions*, $2^{nd}$ ed., Chapter 1, pp. 1–45, 1972; and John Fried and John A. Edwards in *Organic Reactions in Steroid Chemistry*, Chapter 3, pp. 111–145, 1972) in a solvent such as toluene from 15–2000 psi (which is about 1 to about 133 atm) $H_2$ at room temperature to 100° C. The resulting intermediate of formula B-2 is then reacted with an acid, such as p-toluenesulfonic acid, in acetone or is reacted using various literature methods such as those described in *Protecting Groups in Organic Synthesis*, Third Edition, T. W. Greene and P. G. M. Wuts, John Wiley and Sons, Inc. (1999), to yield the compound of formula A-5 of Scheme A wherein $R_x$ is halogen, methyl ether or hydroxy and $R_2$ is defined in the Summary above.

Alternatively, as shown in Scheme B, for example, the compound of fomula A-4 from Scheme A, wherein $R_x$ is halogen, methyl ether or hydroxy and $R_2$ is defined in the Summary above, is reacted with triethylorthoformate and p-toluenesulfonic acid or HCl in ethanol or toluene to form an enol ether intermediate of formula B-3 wherein $R_{a1}$ is ethyl or other acyclic or cyclic lower alkyl or acyl group, depending on the reagent used, and $R_2$ is defined in the Summary above. Alternatively, this enol ether intermediate may be prepared by other literature methods such as those described in *Protecting Groups in Organic Synthesis*, Third Edition, T. W. Greene and P. G. M. Wuts, John Wiley and Sons, Inc. (1999).

Preferably, the compound of formula B-3 wherein $R_x$ is, for example, bromide and the other variables are as defined above is reacted with a strong base such as n-butyl lithium, lithium diisopropylamide, lithium bis(trimethylsilyl)amide, potassium bis(trimrthylsilyl)amide, potassium t-butoxide or others in an aprotic solvent, such as DMF or THF, and $B(OiPr)_3$ or other boron reagents known in the art, at −78° C. to room temperature, depending on the nature of the base used. The boron intermediate thus obtained is treated with a base, such as NaOH, and then a peroxide, such as hydrogen peroxide, to give the compound of formula B-3 wherein $R_x$ is, for example, hydroxy and the other variables are as defined above.

The enol ether intermediate of formula B-3 is then hydrogenated using Pd on $CaCO_3$ or $K_2CO_3$ or other reagents such as platinum oxide or rhodium on aluminum oxide (see P. N. Rylander in *Hydrogenation Methods*, Academic Press, New York, 1985, Herbert O. House in *Modern Synthetic Reactions*, $2^{nd}$ ed., Chapter 1 pp. 1–45, 1972; and John Fried and John A. Edwards in "Organic Reactions in Steroid Chemistry," Chapter 3, pp. 111–145, 1972) in a variety of solvents including ethanol, methanol, THF or ethyl acetate at 15–60 psi (about 1–4 atm) $H_2$ pressure. The resulting intermediate of formula B-4 is then reacted with an acid such as aqueous HCl, in a solvent such as ethanol, or THF or is reacted under other literature conditions, such as those described in *Protecting Groups in Organic Synthesis*, Third Edition, T. W. Greene and P. G. M. Wuts, John Wiley and Sons, Inc. (1999), to yield the compound of formula A-5 of Scheme A wherein $R_5$ is halogen, methyl ether or hydroxy and $R_2$ is defined in the Summary above.

Alternatively, in Scheme B, the compound of formula A-5 is prepared from the compound of formula A-4 by other reported reduction methods, some of which are described in P. Jankowski, S. Marczak, J. Wicha, *Tetrahedron*, 1998, 12071–12150.

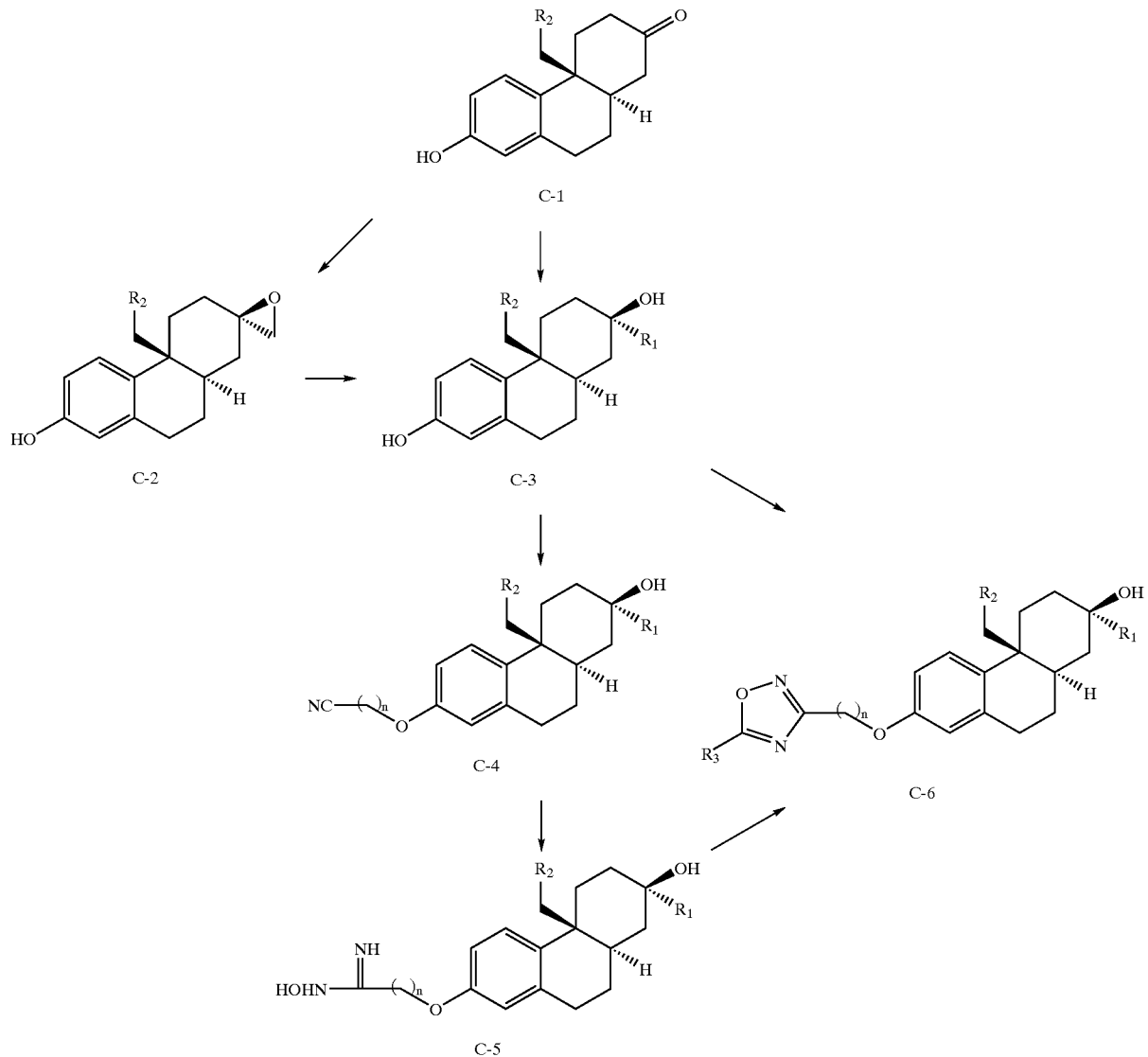

SCHEME C

Scheme C

The compound of formula C-1, which is prepared as the compound of formula A-5 in Scheme A wherein $R_x$ is hydroxy, is reacted with trimethylsulfonium iodide (($CH_3$)$_3$ $S^+I^-$) and a base such as potassium t-butoxide in an aprotic solvent such as DMF to give the compound of formula C-2 wherein $R_2$ is defined in the Summary above. Alternatively, the compound of formula C-2 is obtained from the compound of formula C-1 by other methods described in *Comprehensive Organic Transformations*, $2^{nd}$ ed., R. C. Larock, VCH Publishers Inc. (1999), pp. 944–947.

The compound of formula C-1 is reacted with $R_1$-Metal, such as $R_1$Li, $R_1$MgBr or $R_1$MgCl, wherein $R_1$ is, for example, alkynyl or alkyl, in an aprotic solvent such as THF at low temperature to give the desired isomer of formula C-3 wherein $R_1$ is alkynyl or alkyl and $R_2$ is defined in the Summary above.

Alternatively, the compound of formula C-1 is reacted with trimethylsilyltrifluoromethyl (TMSCF$_3$) and t-butylammoniumfluoride (TBAF) or cesium fluoride (CsF), as described in G. A. Olah et al., *J.Am.Chem.Soc.* (1989) 111, 393, to give the compound of formula C-3 wherein $R_1$ is —CF$_3$ and $R_2$ is defined in the Summary above. Alternatively, the compound of formula C-1 is treated with other —CF$_3$ nucleophiles which are known and available in the literature including, but not limited to, that disclosed by J. Russell, N. Roques, Tetrahedron, 1998, 54, 13771–13782.

Alternatively, the compound of formula C-2 wherein $R_2$ is defined in the Summary above, is reacted with $R_1$-Metal, such as $R_1$Li, $R_1$MgBr, or $R_1$MgCl, wherein $R_1$ is, for example, alkyl, in an aprotic solvent such as THF at low temperature to give the compound of formula C-3 wherein $R_1$ is, for example, —CH$_2$-alkyl and $R_2$ is defined in the Summary above. Alternatively, the compound of formula C-2 wherein $R_2$ is defined in the Summary above is reacted with lithium aluminum hydride or other hydride donors in an aprotic solvent such as THF, at room temperature to the refluxing temperature of the solvent used, to give the compound of the formula C-3 wherein $R_1$ is, for example, methyl, and $R_2$ is defined in the Summary above.

Alternatively, the compound of formula C-2 wherein $R_2$ is defined in the Summary above is reacted with $R_1$—O—Metal, such as $R_1$ONa, $R_1$OK, $R_1$OLi, wherein $R_1$ is, for example, alkyl, in an aprotic solvent such as THF, at room temperature to the refluxing temperature of the solvent used, to give the compound of the formula C-3 wherein $R_1$ is, for example, —CH$_2$—O-alkyl and $R_2$ is defined in the Summary above.

The compound of formula C-3 wherein $R_1$ is alkynyl and $R_2$ is defined in the Summary above is reacted with $H_2$, Pd/C or PtO$_2$ to give the corresponding saturated alkyl product.

The compound of formula C-3 wherein the variables are as defined above is reacted with a base such as NaH, t-butoxide or Et$_3$N in an aprotic solvent such as DMF or CH$_3$CN at a temperature which is between room temperature and 200° C. depending on the nature of the solvent used, and is then reacted with an alkylating agent of formula NC—$R_b$—V wherein $R_b$ is, for example, alkyl and V is a leaving group to give the compound of formula of C-4.

The compound of formula C-4 wherein n is, for example, one to three is reacted with a hydroxyamine or its HCl salt in a protic solvent, such as ethanol or methanol, and a base such as $K_2CO_3$ at a temperature between room temperature and 150° C. depending on the nature of the solvent used, to give the compound of formula C-5 wherein n is one to three, for example.

The amidoxime of formula C-5 is then reacted with an acetylating agent such as carboxylic acid chloride, anhydride, or alkyl ester and a base such as pyridine in an aprotic solvent such as DMF to give the 1,2,4-oxadiazole compound of formula C-6.

Alternatively, the 1,2,4-oxadiazole compound of formula C-6 can be obtained by reacting a compound of formula C-3 with a compound of formula Y, wherein X is a halogen or a leaving group such as tosylate or mesylate, n is, for example, one to three, and the other variables are as defined above, in the presence of a base and in an aprotic solvent.

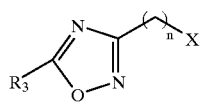

It has also been found that the compounds of the present invention have improved physical and/or chemical properties, which would be beneficial in manufacturing and/or formulating these compounds.

Some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection and the use of such protection/deprotection is readily determined by one skilled in the art. For a general description of protecting groups and their use, see T. W. Greene, *Protective Groups in Organic Synthesis*, Third Edition, John Wiley & Sons, New York, 1999.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds and of said prodrugs, which contain the aforementioned isotopes and/or other isotopes of other atoms are within the scope of this invention. Certain isotopically-labelled compounds of the present invention, for example those into which radioactive isotopes such as $^3$H or $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes, Preparations and/or Examples below, by substituting a readily available isotopically labelled reagent for a non-isotopically labelled reagent.

Any of the compounds and prodrugs of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, sulfonic, citric, camphoric, maleic, acetic, lactic, nicotinic, nitric, succinic, phosphoric, malonic, malic, salicyclic, phenylacetic, stearic, palmitic, pyridine, ammonium, piperazine, diethylamine, nicotinamide, formic, fumaric, urea, sodium, potassium, calcium, magnesium, zinc, lithium, cinnamic, methylamino, methanesulfonic, picric, p-toluenesulfonic, naphthalenesulfonic, tartaric, triethylamino, dimethylamino, and tris(hydroxymethyl)aminomethane. Additional pharmaceutically acceptable salts would be apparent to one of ordinary skill in the art. Where more than one basic moiety exists, the expression includes multiple salts (e.g., di-salt).

Some of the compounds of the present invention are basic and they form a salt with a pharmaceutically acceptable anion. All such salts, including di-salts, are within the scope of the present invention and can be prepared by conventional methods. They can be prepared simply by contacting the basic entities, in either an aqueous, non-aqueous or partially aqueous medium. For example, the mesylate salt is prepared by reacting the free base form of the compound of Formula I with methanesulfonic acid under standard conditions. Likewise, the hydrochloride salt is prepared by reacting the free base form of the compound of Formula I with hydrochloric acid under standard conditions. The salts are recovered by filtration, by precipitation with a non-solvent followed by filtration, by evaporation of the solvent or, in the case of aqueous solutions, by lyophilization, as appropriate.

In addition, when the compounds of the present invention, including prodrugs and salts thereof, form hydrates or solvates, they are also within the scope of the present invention.

The compounds of the present invention, including prodrugs and salts thereof, may also include racemates, stereoisomers and mixtures of these compounds, including isotopically-labeled and radio-labeled compounds. Such isomers can be isolated by standard resolution techniques, including fractional crystallization and chiral column chromatography.

For instance, the compounds of the present invention have asymmetric carbon atoms and are therefore enantiomers or diastereomers. Diasteromeric mixtures can be separated into their individual diastereomers on the basis of their physical/chemical differences by methods known in the art, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered to be part of the present invention.

The following configuration of the compounds of the present invention (as represented by simplified structures) is preferred:

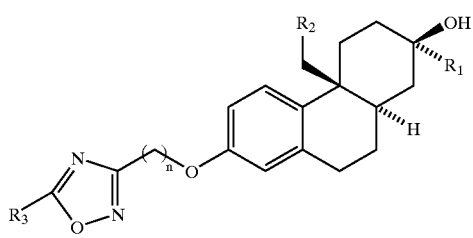

Also, the compounds of the present invention, and any isomers, prodrugs and pharmaceutically acceptable salts thereof, can exist in several tautomeric forms, including the enol form, the keto form and mixtures thereof. All such tautomeric forms are included within the scope of the present invention.

The GR agonists, partial agonists and antagonists of the present invention modulate glucocorticoid receptor-mediated diseases. As such, these compounds can be used to influence the basic, life sustaining systems of the body, including carbohydrate, protein and lipid metabolism, electrolyte and water balance, and the functions of the cardiovascular, kidney, central nervous, immune, skeletal muscle and other organ and tissue systems. In this regard, GR modulators are used for the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's disease and Parkinson's disease), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty.

The present invention relates to methods of treating disorders such as the following: endocrine disorders (such as primary or secondary adrenocortical insufficiency; congenital adrenal hyperplasia, nonsuppurative thyroiditis and hypercalcemia associated with cancer); arthritis (such as osteoarthritis; psoriatic arthritis; rheumatoid arthritis; juvenile rheumatoid arthritis; ankylosing spondylitis; acute and subacute bursitis; acute nonspecific tenosynovitis; acute gouty arthritis; post-traumatic osteoarthritis; synovitis of osteoarthritis and epicondylitis); collagen diseases (such as exacerbation or as maintenance therapy in systemic lupus erythematosus, acute rheumatic carditis and systemic dermatomyositis (polymyositis)); dermatologic diseases (such as pemphigus, bullous dermatitis herpetiformis, erythema multiforme, Stevens-Johnson syndrome, exfoliative dermatitis, mycosis fungoides; psoriasis and seborrheic dermatitis); allergic states (such as control of severe or incapacitating allergic conditions intractable to adequate trials of conventional treatment, rhinitis including seasonal or perennial allergic rhinitis, asthma including bronchial asthma, contact dermatitis, atopic dermatitis, serum sickness, food allergies and drug hypersensitivity reactions); ophthalmic diseases (such as the treatment of severe acute and chronic allergic and inflammatory processes involving the eye and its adnexa, such as allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis and sympathetic ophthalmia); respiratory diseases (such as chronic obstructive pulmonary disease, acute respiratory distress syndrome, symptomatic sarcoidosis, Loeffler's syndrome; berylliosis, fulminating or disseminated pulmonary tuberculosis and aspiration pneumonitis); hematologic disorders (such as idiopathic thrombocytopenic purpura, secondary thrombocytopenia, acquired (autoimmune) hemolytic anemia, erythroblastopenia (RBC anemia) and congenital (erythroid) hypoplastic anemia); neoplastic diseases (such as leukemias and lymphomas); edematous states (such as to induce a diuresis or remission of proteinuria in the nephrotic syndrome, without uremia, of the idiopathic type or that due to lupus erythematosus); gastrointestinal diseases (such as ulcerative colitis, inflammatory bowel diseases, Crohns disease and regional enteritis); tuberculous, tuberculous meningitis, trichinosis with neurologic or myocardial involvement, immunomodulation such as graft vs. host transplant rejection, multiple sclerosis, glucocorticoid insufficiency and systemic fungal infections, in a mammal comprising administering to said mammal a therapeutically effective amount of a compound of Formula I.

The compounds of the present invention, and prodrugs and pharmaceutically acceptable salts thereof, are useful to induce weight loss in mammals needing or desiring to lose weight. While not intending to limit the present invention to a specific mechanism of action, the compounds of the present invention, and prodrugs and salts thereof, are able to induce weight loss by a variety of mechanisms, such as appetite suppression, decreasing food intake and stimulation of the metabolic rate in peripheral tissue, thereby increasing energy expenditure. In addition, the compounds of the present invention, prodrugs and salts thereof are useful to induce a more favorable partitioning of nutrients from fat to muscle tissue in mammals. Thus, while not necessarily resulting in weight loss, this increase in muscle mass may be useful in preventing or treating diseases, such as obesity and frailty.

In addition, the compounds of the present invention, prodrugs and pharmaceutically acceptable salts thereof, may also be useful to increase lean meat deposition, improve lean meat to fat ratio, and trim unwanted fat from non-human animals, as described further below.

It will be understood by those skilled in the art that while the compounds of the present invention, prodrugs and pharmaceutically acceptable salts thereof, will typically be employed as selective agonists, partial agonists or antagonists, there may be instances where a compound with a mixed steroid receptor profile is preferred.

The pharmaceutical compositions and compounds of the present invention, including prodrugs and pharmaceutically acceptable salts thereof, will generally be administered daily in the form of a dosage unit (e.g., tablet, capsule, etc.) at a therapeutically effective amount of such compound, prodrug or salt thereof from about 0.1 µg/kg of body weight to about 500 mg/kg of body weight, more particularly from about 1 µg/kg to about 250 mg/kg, and most particularly from about 2 µg/kg to about 100 mg/kg. More preferably, a compound of the present invention will be administered at an amount of about 0.1 mg/kg to about 500 mg/kg of body weight, and most preferably from about 0.1 mg/kg to about 50 mg/kg of body weight. As recognized by those skilled in the art, the particular quantity of pharmaceutical composition according to the present invention administered to a patient will depend upon a number of factors, including, without limitation, the activity desired, the condition of the patient, and tolerance for the compound.

Furthermore, it will be understood by those skilled in the art that the compounds, prodrugs and pharmaceutically acceptable salts thereof, including pharmaceutical compositions and formulations containing these compounds, prodrugs and salts can be used in a wide variety of combination therapies to treat the conditions and diseases described above. Thus, the compounds, prodrugs and pharmaceutically acceptable salts thereof of the present invention can be used in conjunction with (e.g., simultaneously or sequentially) other pharmaceutical agents for the treatment of the disease/conditions described herein. For example, they may be used in combination with pharmaceutical agents that treat obesity, diabetes, inflammatory disease, immunodefficiency, hypertension, cardiovascular disease, viral infection, HIV, Alzheimers's disease, Parkinson's disease, anxiety, depression, or psychosis. In combination therapy treatment, both the compounds, prodrugs and pharmaceutically acceptable salts thereof of this invention and the other drug therapies are administered to mammals (e.g., humans, male or female) by conventional methods.

For instance, glucocorticoid receptor agonists are efficacious agents for the treatment of various inflammatory diseases; however, treatment is often accompanied by undesirable side effects. These side effects include, but are not limited to, the following examples: metabolic effects, weight gain, muscle wasting, decalcification of the skeleton, osteoporosis, thinning of the skin and thinning of the skeleton. However, according to the present invention, glucocorticoid receptor modulators may be used in combination with glucocorticoid receptor agonists to block some of these side effects, without inhibiting the efficacy of the treatment. Thus, any glucocorticoid receptor agonist may be used as the second compound in the combination aspect of the present invention. This combination includes the treatment of various inflammatory diseases, such as arthritis (osteo and rheumatoid), asthma, rhinitis, or immunomodulation. Examples of glucocorticoid receptor modulators include those known in the art (many of which are described above) as well as the compounds of the present invention. More particularly, examples of glucocorticoid receptor modulators known in the art include, but are not limited to, certain nonsteroidal compounds, such as 5H-chromeno[3,4-f] quinolines, which are selective modulators of steroid receptors, as disclosed in U.S. Pat. No. 5,696,127; and certain steroid compounds which possess antiglucocorticoid activity, and some of which have glucocorticoid activity, as disclosed in Published European Patent Application 0 188 396, published 23 Jul. 1986. Examples of glucocorticoid receptor agonists include those known in the art, such as prednisone (17,21-dihydroxypregnane-1,4-diene-3,11,20-trione), prednylidene ((11β)-11,17,21-trihydroxy-16-methylenepregna-1,4-diene-3,20-dione), prednisolone ((11β)-11,17,21-trihydroxypregna-1,4-diene-3,20-dione), cortisone (17α,21-dihydroxy-4-pregnene-3,11,20-trione), dexamethasone ((11β, 16α)-9-fluoro-11,17,21-trihydroxy-16-methylpregna-1,4-diene-3,20-dione), and hydrocortisone (11β,17α,21-trihydroxypregn-4-ene-3,20-dione). These compounds which are glucocorticoid receptor agonists will generally be administered in the form of a dosage unit at a therapeutically effective amount of such compound. For example, prednisone or an equivalent compound may be administered from about 5 to about 80 mg, depending on the condition; hydrocortisone may be administered from about 100 to about 400 mg, depending on the condition; and dexamethasone may be administered from about 4 to about 16 mg, depending on the condition. These doses are typically administered once to twice daily, and for maintenance purposes, sometimes on alternate days.

For the treatment of Alzheimer's disease, any cholinomimetic drug, such as donepezil hydrochloride (ARICEPT®), may be used as the second compound in the combination aspect of this invention.

For the treatment of Parkinson's disease, any anti-Parkinson's drug, such as L-dopa, bromocriptine, or selegiline, may be used as the second compound in the combination aspect of this invention.

For the treatment of anxiety, any antianxiolytic drug, such as benzodiazepine, valium, or librium, may be used as the second compound in the combination aspect of this invention.

For the treatment of depression, any tricyclic antidepressant such as, desipramine, or any selective serotonin reuptake inhibitor (SSRI's), such as sertraline hydrochloride or fluoxetine hydrochloride, may be used as the second compound in the combination aspect of this invention.

For the treatment of psychosis, any typical or atypical antipsychotic drug, such as haloperidol or clozapine may be used as the second compound in the combination aspect of this invention.

For the treatment of diabetes, any aldose reductase inhibitor may be used as the second compound in the combination aspect of this invention. The term aldose reductase inhibitor refers to a compound, which inhibits the bioconversion of glucose to sorbitol catalyzed by the enzyme aldose reductase. Such inhibition is readily determined by those skilled in the art according to standard assays (J. Malone, Diabetes, 29:861–864, 1980, "Red Cell Sorbitol, an Indicator of Diabetic Control"). A variety of aldose reductase inhibitors are described and referenced below; however other aldose reductase inhibitors will be known to those skilled in the art. Examples of aldose reductase inhibitors include compounds such as those disclosed and described in WO 99/43663, published 2 Sep. 1999.

Any glycogen phosphorylase inhibitor may be used as the second compound in the combination aspect of this invention. The term glycogen phosphorylase inhibitor refers to any substance or agent or any combination of substances and/or agents which reduces, retards or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described in WO 99/43664, published 2 Sep. 1999). A variety of these compounds are described in the following published international patent applications: WO 96/39384, published 12 Dec. 1996, WO 96/39385, published 12 Dec. 1996, and WO 99/43663, published 2 Sep. 1999.

Any sorbitol dehydrogenase inhibitor may be used as the second compound in the combination aspect of this invention. The term sorbitol dehydrogenase inhibitor refers to a compound which inhibits the enzyme sorbitol dehydrogenase, which catalyzes the oxidation of sorbitol to fructose. Such inhibition is readily determined by those skilled in the art according to standard assays (as described in U.S. Pat. No. 5,728,704 and references cited therein). A variety of these compounds are described and referenced below; however other sorbitol dehydrogenase inhibitors will be known to those skilled in the art. U.S. Pat. No. 5,728,704 discloses substituted pyrimidines which inhibit sorbitol dehydrogenase, lower fructose levels, and/or treat or prevent diabetic complications, such as diabetic neuropathy, diabetic retinopathy, diabetic nephropathy, diabetic microangiopathy and diabetic macroangiopathy.

Any known, commercially marketed antidiabetic compound may be used as the second compound in the combination aspect of this invention. A variety of such compounds are described and referenced below; however other such compounds will be known to those skilled in the art. Examples of such compounds useful in the compositions and methods of this invention include, for example, insulin, inhaled insulin, metformin, and sulfonylureas, such as glipazide (GLUCOTROL®), glyburide (GLYNASE®, MICRONASE®) and chlorpropamide (DIABINASE®).

Any β-adrenergic agonist may be used as the second compound in the combination aspect of this invention. β-Adrenergic agents have been categorized into $\beta_1$, $\beta_2$, and $\beta_3$ subtypes. Agonists of β-receptors promote the activation of adenyl cyclase. Activation of $\beta_1$ receptors invokes increases in heart rate. Activation of $\beta_2$ receptors induces relaxation of smooth muscle tissue which produces a drop in blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate $\beta_3$ receptors are therefore useful as anti-obesity agents. Compounds which are $\beta_3$-receptors agonists have hypoglycemic and/or anti-diabetic activity. Such activity is readily determined by those skilled in the art according to standard assays (International Patent Application, Publication No. WO 96/35671). Several compounds are described and referenced below; however, other β-adrenergic agonists will be known to those skilled in the art. International Patent Application, Publication No. WO 96/35671 discloses compounds, such as substituted aminopyridines, which are β-adrenergic agonists. International Patent Application, Publication No. 93/16189 discloses the use of selective $\beta_3$ receptor agonists in combination with compounds which modify eating behavior for the treatment of obesity.

Any thyromimetic antiobesity agent may be used as the second compound in the combination aspect of this invention. These compounds are tissue selective thyroid hormone agonists. These compounds are able to induce weight loss by mechanisms other than appetite suppression, e.g., through stimulation of the metabolic rate in peripheral tissue, which, in turn, produces weight loss. Such metabolic effect is readily measured by those skilled in the art according to standard assays. A variety of these compounds will be known to those skilled in the art. It is well known to one of ordinary skill in the art that selectivity of the thermogenic effect is an important requirement for a useful therapeutic agent in the treatment of, for example, obesity and related conditions.

Any eating behavior modifying compound may be used as the second compound of this invention. Compounds which modify eating behavior include anorectic agents, which are compounds that diminish the appetite. Such classes of anorectic agents are well known to one of ordinary skill in the art. A variety of these compounds which are anorectic agents will be known to those skilled in the art. Also, the following are antiobesity agents: phenylpropanolamine, ephedrine, pseudoephedrine, phentermine, a Neuropeptide Y (hereinafter also referred to as "NPY") antagonist, a cholecystokinin-A (hereinafter referred to as CCK-A) agonist, a monoamine reuptake inhibitor (such as sibutramine), a sympathomimetic agent, a serotoninergic agent (such as fenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a galanin antagonist or a GI lipase inhibitor or decreaser (such as orlistat). Other antiobesity agents include phosphatase 1B inhibitors, bombesin agonists, dehydroepiandrosterone or analogs thereof, glucocorticoid receptor antagonists, orexin receptor antagonists, urocortin binding protein antagonists or glucagon-like peptide-1 (insulinotropin) agonists. A particularly preferred monoamine reuptake inhibitor is sibutramine, which can be prepared as disclosed in U.S. Pat. No. 4,929,629. Preferred serotoninergic agents include fenfluramine and fenfluramine, which can be prepared as disclosed in U.S. Pat. No. 3,198,834. A particularly preferred dopamine agonist is bromocriptine, which can be prepared as disclosed in U.S. Pat. Nos. 3,752,814 and 3,752,888. Another preferred anorectic agent is phentermine, which can be prepared as disclosed in U.S. Pat. No. 2,408,345.

Any NPY receptors antagonist may be used as the second component in the combination aspect of this invention. The term NPY receptors antagonist refers to compounds which interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays (such as those described in International Patent Application, Publication No. WO 99/07703). In addition, the compounds described and referenced below are NPY receptors antagonists; however, other NPY receptors antagonists will also be known to those skilled in the art. International Patent Application, Publication No. WO 99/07703 discloses certain 4-aminopyrrole (3,2-d) pyrimidines as neuropeptide Y receptor antagonists. International patent application, Publication No. WO 96/14307, published 17 May 1996; International patent application, Publication No. WO 96/40660, published 19 Dec. 1996; International patent application, Publication No. WO 98/03492; International patent application, Publication No. WO 98/03494;

International patent application, Publication No. WO 98/03493; International patent application, Publication No. WO 96/14307, published 17 May 1996; International patent application, Publication No. WO 96/40660, published 19 Dec. 1996; disclose additional compounds, such as substituted benzylamine derivatives, which are useful as neuropeptide Y receptors specific ligands.

The disclosure of each of the references, patents and published applications cited within this description are hereby incorporated by reference herein.

In combination therapy treatment, both the compounds of this invention and the other compound therapies are administered to mammals (e.g., humans, male or female) by conventional methods. As recognized by those skilled in the art, the therapeutically effective amounts of the compounds of this invention and the other compound therapies to be administered to a patient in combination therapy treatment will depend upon a number of factors, including, without limitation, the biological activity desired, the condition of the patient, and tolerance for the compound.

For example, the second compound of this invention, when administered to a mammal, is dosed at a range between about 0.01 to about 50 mg/kg/day body weight, preferably about 0.1 mg/kg/day to about 10 mg/kg/day body weight, administered singly or as a divided dose. Particularly, when the second compound of this invention is (1) sibutramine, the dosage of sibutramine is about 0.01 mg/kg/day to about 30 mg/kg/day body weight, preferably about 0.1 mg/kg/day to about 1 mg/kg/day body weight; (2) fenfluramine, the dosage of fenfluramine is about 0.01 mg/kg/day to about 30 mg/kg/day body weight, preferably about 0.1 mg/kg/day to about 1 mg/kg/day body weight; (3) bromocriptine, the dosage of bromocriptine is about 0.01 to about 10 mg/kg/day body weight, preferably 0.1 mg/kg/day to about 10 mg/kg/day body weight; (4) phentermine, the dosage of phentermine is about 0.01 mg/kg/day to about 10 mg/kg/day, preferably about 0.1 mg/kg/day to about 1 mg/kg/day body weight. Also, for example, as noted above, an amount of an aldose reductase inhibitor that is effective for the activities of this invention may be used as the second compound of this invention. Typically, an effective dosage for aldose reductase inhibitors for this invention is in the range of about 0.1 mg/kg/day to about 100 mg/kg/day in single or divided doses, preferably about 0.1 mg/kg/day to about 20 mg/kg/day in single or divided doses.

As noted above, the compounds, prodrugs and pharmaceutically acceptable salts of the present invention can be combined in a mixture with a pharmaceutically acceptable carrier, vehicle or diluent to provide pharmaceutical compositions useful for treating the conditions or disorders noted herein in mammalian, and more preferably, in human, patients. The particular carrier, vehicle or diluent employed in these pharmaceutical compositions may take a wide variety of forms depending upon the type of administration desired, for example, intravenous, oral, topical, suppository or parenteral. Also, the compounds, prodrugs and salts thereof of this invention can be administered individually or together in any conventional dosage form, such as an oral, parenteral, aerosol, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds, prodrugs and pharmaceutically acceptable salts thereof of this invention can be combined with various sweetening agents, flavoring agents, coloring agents, emulsifying agents and/or suspending agents, as well as such diluents as water, ethanol, propylene glycol, glycerin and various like combinations thereof.

Due to their ease of administration, tablets and capsules represent the most advantageous oral dosage form for the pharmaceutical compositions of the present invention.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

For topical administration, the compounds, prodrugs and pharmaceutically acceptable salts thereof of the present invention may be formulated using bland, moisturizing bases, such as ointments or creams. Examples of suitable ointment bases are petrolatum, petrolatum plus volatile silicones, lanolin, and water in oil emulsions.

Methods of preparing various pharmaceutical compositions with a certain amount of a compound of Formula I, or a prodrug or salt thereof, are known, or will be apparent in light of this disclosure, to those skilled in this art. For examples of methods of preparing pharmaceutical compositions, see *Remington's Pharmaceutical Sciences*, Mack Publishing Company, Easter, Pa., 19th Edition (1995).

Since the present invention has an aspect that relates to the treatment of the disease/conditions described herein with a combination of compounds which may be administered separately, the invention also relates to combining separate pharmaceutical compositions in kit form. The kit comprises two separate pharmaceutical compositions: a compound of formula I, a prodrug thereof or a salt of such compound or prodrug, and a second compound as described above. The kit comprises a container, such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of formula I compound (or a prodrug or pharmaceutically acceptable salt thereof) can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The following paragraphs describe exemplary formulations, dosages etc. useful for non-human animals. The administration of compounds of this invention (optionally in conjunction with other pharmaceutical agents as described above) can be effected orally or non-orally, for example by injection. An amount of a compound of formula I, a prodrug or pharmaceutically acceptable salt thereof, is administered such that a therapeutically effective dose is received, generally a daily dose which, when administered orally to an animal, is usually between 0.01 and 500 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of agents in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with a proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the present invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

The present invention has several advantageous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

Drinking water and feed effective for increasing lean meat deposition and for improving lean meat to fat ratio are generally prepared by mixing a compound of the present invention with a sufficient amount of animal feed to provide from about $10^{-3}$ to 500 ppm of the compound in the feed or water.

The preferred medicated swine, cattle, sheep and goat feed generally contain from about 1 to 400 grams of active ingredient per ton of feed, the optimum amount for these animals usually being about 50 to 300 grams per ton of feed.

The preferred feed of domestic pets, such as cats and dogs, usually contain about 1 to 400 grams and preferably about 10 to 400 grams of compound per ton of feed.

For parenteral administration in animals, the compounds, prodrugs and pharmaceutically acceptable salts of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of a compound, prodrug and pharmaceutically acceptable salt of the present invention to provide the animal with 0.01 to 500 mg/kg/day of body weight of the compound. The preferred dosage for poultry, swine, cattle, sheep, goats and domestic pets is in the range of from 0.1 to 50 mg/kg/day of body weight of compound.

Paste formulations can be prepared by dispersing a compound of this invention in a pharmaceutically acceptable oil such as peanut oil, sesame oil, corn oil or the like.

Pellets containing an effective amount of a compound, prodrug and pharmaceutically acceptable salt of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper compound level in the animal's body.

The activity of the compounds, prodrugs and pharmaceutically acceptable salts thereof of the present invention are demonstrated by one or more of the assays described below:

The following is a description of an assay for the identification of glucocorticoid receptor modulators having glucocorticoid receptor agonist and/or antagonist activity: HeLa cells containing endogenous human glucocorticoid receptors are transfected with a 3×GRE-luciferase plasmid generated by standard procedures and a plasmid conferring neomycin resistance. Novel glucocorticoid responsive cell lines are generated and characterized. One such cell line designated HeLa-GRE9 is used for determining the activity of compounds at the glucocorticoid receptor. Cells are maintained in charcoal-stripped serum and transferred to 96-well microtiter plates one day prior to treatment with various concentrations ($10^{-12}$ to $10^{-5}$) of test compounds in the absence and presence of known glucocorticoid receptor agonists (i.e., dexamethasone, hydrocortisone) for up to 24 hours. Treatments are performed in triplicate. Cell lysates are prepared and luciferase activity is determined using a luminometer. Agonist activity is assessed by comparing the luciferase activity from cells treated with test compound to cells treated with the agonist, dexamethasone. Antagonist activity is assessed by comparing the luciferase activity of an $EC_{50}$ concentration of dexamethasone in the absence and presence of test compound. The $EC_{50}$ (concentration that produced 50% of the maximal response) for dexamethasone is calculated from dose response curves.

The following is a description of an assay for determining the competitive inhibition binding of the Human Type II Glucocorticoid receptor expressed in Sf9 cells:

Binding protocol: Compounds are tested in a binding displacement assay using human glucocorticoid receptor expressed in Sf9 cells with $^3$H-dexamethasone as the ligand. Human glucorticoid receptor is expressed in Sf9 cells as described in Mol. Endocrinology 4: 209, 1990. Pellets containing Sf9 cells expressing the human GR receptor from 1L vats are lysed with 40 ul of 20 mM AEBSF stock (Calbiochem, LaJolla, Calif.) containing 50 mg/ml leupeptin and 40 ml of homogenization buffer is added. The assay is carried out in 96-well polypropylene plates in a final volume of 130 ul containing 200 ug Sf9 lysate protein, 6.9 nM $^3$H-dexamethasone (Amersham, Arlington Heights, Ill.) in presence of test compounds, test compound vehicle (for total counts) or excess dexamethasone (7 uM non-radioactive, to determine non-specific binding) in an appropriate volume of assay buffer. All compounds are tested at 6 concentrations in duplicate (concentration range 0.1–30 nM or 3–1000 nM). Test compounds are diluted from a 25 mM stock in 100% DMSO with 70% EtOH and added in a volume of 2 $\mu$l. Once all additions are made the plates are shaken, sealed with sealing tape and incubated at 4° C. overnight.

After the overnight incubation, unbound counts are removed with dextran coated charcoal as follows: 75 $\mu$l of dextran coated charcoal (5.0 g activated charcoal, 0.5 g dextran adjusted to volume of 100 ml with assay buffer) is added, plates are shaken and incubated for five minutes at 4° C. Plates are then centrifuged in a refrigerated benchtop centrifuge at top speed for 15 minutes. One hundred pi of the supernatant from each well is placed into a 96-well PET plate with 200 $\mu$l of scintillation cocktail and counted on a beta counter (1450 MicroBetaTrilux, from Wallac, Turku, Finland).

Data analysis: After subtracting non-specific binding, counts bound are expressed as % of total counts. The concentration response for test compounds are fitted to a sigmoidal curve to determine the IC50 (concentration of compound that displaces 50% of the bound counts).

Reagents: Assay Buffer: 2.0 ml 1M Tris, 0.2 ml 0.5 mM EDTA, 77.1 mg DTT, 0.243 g sodium molybdate in a volume of 100 ml water; Homogenization buffer: 2.0 ml 0.5 M $K_2HPO_4$ (pH 7.6), 20 $\mu$l 0.5 M EDTA ( pH 8.0), 77.1 mg DTT, 0.486 g sodium molybdate in a volume of 100 ml water.

The following is a description of an assay for determining receptor selectivity: T47D cells from ATCC containing endogenous human progesterone and mineralocorticoid receptors are transiently transfected with a 3×GRE-luciferase using Lipofectamine Plus (GIBCO-DRL, Gaithersburg, Md.). Twenty-four hours post-transfection cells are maintained in charcoal-stripped serum and transferred to 96-well microtiter plates. The next day cells are treated with various concentrations ($10^{-12}$ to $10^{-5}$) of test compounds in the absence and presence of a known progesterone receptor agonist (progesterone) and a known mineralocorticoid receptor agonist (aldosterone) for up to 24 hours. Treatments are performed in triplicate. Cell lysates are prepared and luciferase activity is determined using a luminometer. Agonist activity is assessed by comparing the luciferase activity from cells treated with compound alone to cells treated with either the agonist progesterone or aldosterone. Antagonist activity is assessed by comparing the luciferase activity of an $EC_{50}$ concentration of progesterone or aldosterone in the absence and presence of compound. The $EC_{50}$ (concentration that produced 50% of maximal response) for progesterone and aldosterone is calculated from dose response curves.

The following is a description of an assay for determining anti-diabetes and anti-obesity activity: The obese, diabetic ob/ob mouse is used to assess the anti-diabetes and anti-obesity activity of the compounds. Six to 10 week old ob/ob male mice (Jackson Labs, Bar Harbor, Me.) are dosed with test compound for 2 to 10 days. Plasma glucose levels are determined by measuring glucose from samples obtained by orbital bleeding. Glucose is quantitated using an Abbott Autoanalyzer (Abbott, Inc., Abbott Park, Ill.). Food intake is monitored on a daily basis by differential weighing.

The following is a description of an assay for determining the ability of a compound to inhibit glucocorticoid agonist induction of liver tyrosine amino transferase (TAT) activity in conscious rats:

Animals: Male Sprague Dawley rats (from Charles River, Wilimington Mass.) (adrenal-intact or adrenalectomized at least one week prior to the screen) b.w. 90 g are used. The rats are housed under standard conditions for 7–10d prior to use in the screen.

Experimental protocol: Rats (usually 3 per treatment group) are dosed with test compound, vehicle or positive control (Ru486) either i.p., p.o., s.c. or i.v. (tail vein). The dosing vehicle for the test compounds is typically one of the following: 100% PEG 400, 0.25% methyl cellulose in water, 70% ethanol or 0.1 N HCl and the compounds are tested at doses ranging from 10 to 125 mg/kg. The compounds are dosed in a volume of 1.0 ml/100 g body weight (for p.o.) or 0.1 ml/100 g body weight for other routes of administration. Ten minutes after the administration of the test compound, the rats are injected with dexamethasone (0.03 mg/kg i.p. in a volume of 0.1 ml/100 g) or vehicle. To prepare the dexamethasone dosing solution, dexamethasone (from Sigma, St. Louis, Mo.) is dissolved in 100% ethanol and diluted with water (final: 10% ethanol:90% water, vol:vol). Groups treated with vehicle-vehicle, vehicle-dexamethasone, and Ru486-dexamethasone are included in each screen. The compounds are tested vs. dexamethasone only. Three hours after the injection of dexamethasone the rats are sacrificed by decapitation. A sample of liver (0.3 g) is excised and placed in 2.7 ml of ice cold buffer and homogenized with a polytron. To obtain cytosol the liver homogenate is centrifuged at 105,000 g for 60 min and the supernatant is stored at −80° C. until analysis. TAT is assayed on 100 ul of a 1:20 dilution of the 105,000 g supernatant using the method of Granner and Tomkins (Methods in Enzymology 17A: 633–637, 1970) and a reaction time of 8–10 minutes. TAT activity is expressed as umol product/min/g liver.

Interpretation: Treatment data are analyzed by using analysis of variance (ANOVA) with protected least significant difference (PLSD) post-hoc analysis. Compounds are considered active in this test if the TAT activity in the group pretreated with compound prior to dexamethasone administration is significantly ($P<0.05$) decreased relative to the TAT activity in the vehicle-dexamethasone treated group.

The following is a description of an assay for determining the effect of a compound on two typical genes that are upregulated during an inflammatory response. This assay, the glucocorticoid inhibition of IL-1 (Interleukin-1) induced MMP-1 (Matrix Metalloproteinase-1) and IL-8 (Interleukin-8) production in human chondrosarcoma cells, is conducted as follows: SW1353 human chondrosarcoma cells (obtained from ATCC) from passage 12 through passage 19 are used in a 96 well format assay. Cells are plated at confluence into 96 well plates in DMEM (Dulbecco's Modified Eagle Medium) with 10% fetal bovine serum and incubated at 37° C., 5% $CO_2$. After 24 hours, serum containing media is removed and replaced with 200 ul/well DMEM containing 1 mg/L insulin, 2 g/L lactalbumin hydrosylate, and 0.5 mg/L ascorbic acid and returned to incubation at 37° C., 5% $CO_2$. The following morning, the serum free media is removed and replaced with 150 ul/well fresh serum free media containing +/−20 ng/ml IL-1 beta, +/−5 nM dexamethasone, +/− compound. All conditions are completed in triplicate using only the inner 60 wells of the 96 well plate. Outside surrounding wells of the plate contain 200 ul of serum free DMEM. Plates are incubated at 37° C., 5% $CO_2$. At 24 hours after addition of IL-1, 25 ul of sample from each well are removed under aseptic conditions for IL-8 production analysis. Samples are stored at −20° C. until time of analysis. IL-8 production is assessed using the Quantikine human IL-8 ELISA kit from R & D Systems (D8050) on samples diluted 60-fold in RD5P Calibrator Diluent, following the manufacturer's protocol. The percent of the average IL-1 control is determined for the average of each of the triplicate samples following subtraction of the average signal from untreated cells. $IC_{50}$'s are determined from log linear plots of the percent of control versus the concentration of inhibitor. At 72 hours after IL-1 addition, the remaining media is removed and stored at −20° C. until time of MMP-1 production analysis. MMP-1 production is assessed via the Bio-Trak MMP-1 ELISA kit from Amersham (RPN2610) on 100 ul of neat sample following the manufacturer's protocol.

The percent of the average IL-1 control is determined for the average of each of the triplicate samples following subtraction of the average signal from untreated cells. $IC_{50}$'s are determined from log linear plots of the percent of control versus the concentration of inhibitor. Dexamethasone has proven to be a good positive control inhibitor of both IL-8 and MMP1 expression ($IC_{50}$=5 nM).

The following compounds of the present invention are preferred:

2-Phenanthrenol, 7-[[5-[(dimethylamino)methyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-;

2-Phenanthrenol, 1,2,3,4,4a,9,10,10a-octahydro-7-[[5-[2-(4-morpholinyl)ethyl]-1,2,4-oxadiazol-3-yl]methoxy]-4a-(phenylmethyl)-2-(trifluoromethyl)-, (2R,4aS,10aR)-;

2-Phenanthrenol, 1,2,3,4,4a,9,10,10a-octahydro-4a-(phenylmethyl)-7-[[5-(1-piperidinylmethyl)-1,2,4-oxadiazol-3-yl]methoxy]-2-(trifluoromethyl)-, (2R,4aS,10aR)-;

2-Phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxy]-2-(1-propynyl)-, (2R,4aS,10aR)-;

2-Phenanthrenol, 1,2,3,4,4a,9,10,10a-octahydro-4a-(phenylmethyl)-2-(1-propynyl)-7-[[5-(1,2,5,6-tetrahydro-1-methyl-3-pyridinyl)-1,2,4-oxadiazol-3-yl]methoxy]-, (2R,4aS,10aR)-;

2-Phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-propyl-, (2R,4aS,10aR)-;

2-Phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-propyl-, (2R,4aS,10aR)-;

2-Phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxyl-2-propyl-, (2R,4aS,10aR)-;

2-Phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-propyl-, (2R,4aS,10aR)-;

2-Phenanthrenol, 1,2,3,4,4a,9,10,10a-octahydro-4a-(phenylmethyl)-7-[[5-(1-piperidinylmethyl)-1,2,4-oxadiazol-3-yl]methoxy]-2-propyl-, (2R,4aS,10aR)-;

2-Phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-;

2-Phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-(trifluoromethyl)-, (2R,4aS,10aR)-;

2-Phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxy]-2-(trifluoromethyl)-, (2R,4aS,10aR)-;

2-Phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-;

2-Phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-(1-propynyl)-, (2R,4aS,10aR)-;

2-Phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-(1-propynyl)-, (2R,4aS,10aR)-;

2-Phenanthrenol, 7-[[5-[2-(diethylamino)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-; and 2-Phenanthrenol, 7-[[5-methyl]-1,2,4-oxadiazol-3-yl] methoxy]-1,2,3,4,4a,9,10,10a-octahydro-4a-(phenylmethyl)-2-(trifluoromethyl)-, (2R,4aS,10aR)-.

EXAMPLES

Preparation 1

1-Benzyl-6-methoxy-3,4-dihydro-1H-naphthalen-2-one

A solution of 51 g (0.289 mol) of 6-methoxy-2-tetralone of formula A-1 wherein $R_x$ is methoxy, and 24.2 mL (0.289 mol) of pyrrolidine in 1.5 L of toluene was heated to reflux, over a Dean-Stark trap, overnight. After removal of the azeotroped water, the reaction mixture was cooled to RT, concentrated to an oil, and dissolved in 725 mL of dioxane. To this solution was added 52 mL (0.434 mol) of benzyl bromide and the resulting solution was heated to reflux overnight. Water (100 mL) was added to the solution, and the resultant mixture was heated to reflux for an additional 2 h. The mixture was cooled to room temperature and poured into a solution of 1 N HCl and extracted 3 times with EtOAc. The organic layers were washed with $H_2O$ and saturated $NaHCO_3$, then dried over $Na_2SO_4$, filtered, and evaporated to dryness. The crude product was purified by flash chromatography over $SiO_2$ using 10% EtOAc to 15% EtOAc in hexanes as the gradient eluant to give 65.2 g of the title product of this preparation as a yellow oil (85%). IR (neat) 2937, 1712, 1500 $cm^{-1}$; $^1H$ NMR (400 MHz, $CDCl_3$) δ 2.41–2.59 (m, 3H), 2.76 (dt, 1H, J=5.4, 15.5), 3.15–3.70 (m, 2H), 3.67 (t, 1H, J=6.3), 3.77 (s, 3H), 6.67–6.70 (m, 2H), 6.81 (d, 1H, J=8.1), 6.87–6.89 (m, 2H), 7.13–7.17 (m, 3H); $^{13}C$ NMR (100 MHz, $CDCl_3$) δ 27.44, 38.19, 39.19, 54.13, 55.14, 112.11, 112.96, 126.30, 128.07, 128.26, 129.35, 129.53, 138.05, 138.20, 158.30, 212.41; MS m/z 267 $(M+H)^+$.

Preparation 2

1(R)-Benzyl-6-methoxy-1(S)-(3-oxo-butyl)-3,4-dihydro-1H-naphthelen-2-one

A solution of 62 g (0.23 mol) of the title product of Preparation 1 and 28 mL, (0.23 mol) of freshly distilled (S)-(−)-α-methyl benzylamine in 100 mL of toluene was heated to reflux, over a Dean-Stark trap, overnight. After removal of the azeotroped water, the imine solution was cooled to 0° C. and 21 mL (0.26 mol) of freshly distilled methylvinylketone was added dropwise to the solution. The solution was stirred at 0° C. for 30 min then heated to 40° C. overnight. The reaction solution was cooled to 0° C. and 17 mL of acetic acid and 14 mL of $H_2O$ were added and the resultant solution was allowed to warm to RT for 2 h. The solution was poured into $H_2O$ and extracted three times with EtOAc. The combined organic layers were washed with 1 N HCl, $H_2O$, saturated $NaHCO_3$, then dried over $Na_2SO_4$, filtered, and evaporated to dryness. The crude product was purified by chromatography over $SiO_2$ using 15% EtOAc to 35% EtOAc in hexanes as the gradient eluant to give 48 g of the title product of this preparation as a yellow solid. $^1HNMR$ (400 MHz, $CDCl_3$) δ 1.38 (s, 3H), 1.40–1.51 (m, 2H), 1.64 (ddd, 1H, J=2.1, 4.5, 13), 1.97 (broad s, 1H), 2.20 (dt, 1H, J=4.5, 13), 2.59 (d, 1H, J=6.6), 3.08 (d, 1H, J=18), 3.16 (d, 1H, J=16), 3.33 (dd, 1H, J=6.6, 18), 3.62 (d, 1H, J=16), 3.72 (s, 3H), 6.57 (d, 1H, J=2.5), 6.67 (dd, 1H, J=2.5, 8.8), 7.00–7.23 (m, 6H); $^{13}C$ NMR (100 MHz, $CDCl_3$) δ 27.90, 32.79, 34.40, 38.43, 41.49, 53.51, 55.12, 58.47, 79.06, 112.05, 113.09, 125.37, 127.63, 127.69, 130.27, 132.21, 135.45, 138.65, 157.88, 213.49; MS m/z337 $(M+H)^+$, 319 $(M-OH)^+$.

Preparation 3

2(3H)-Phenanthrenone, 4,4a,9,10-tetrahydro-7-methoxy-4a-(phenylmethyl)-, (S)—

A solution of 48 g (143 mmol) of the title product of Preparation 2 and 71 mL of 1 M sodium methoxide in 100 mL of methanol was stirred at room temperature for 15 min, then heated to 75° C. for 3 h. The solution was cooled to 0° C., 8.2 mL of acetic acid was added dropwise, and the solution was concentrated to an oil. The oil was dissolved in EtOAc, washed with saturated $NaHCO_3$ and brine, dried over $Na_2SO_4$, filtered, and evaporated to dryness. The crude product was purified by chromatography over $SiO_2$ using 15% EtOAc to 35% EtOAc in hexanes as the gradient eluant to give 44 g of the title product of this preparation as an off-white powder (60% from 1-benzyl-6-methoxy-3,4-dihydro-1H-naphthalen-2-one). Recrystallization from EtOAc/hexane afforded 35 g of the title product of this preparation as a white crystalline solid. mp 101–102° C.; IR (neat) 1667, 1500 $cm^{-1}$; $^1HNMR$ ($CDCL_3$) 1.83–1.90 (m, 1H), 2.02 (dt, 1H, J=5.5, 14), 2.27 (dt, 1H, J=4.3, 14) 2.44–2.51 (m, 2H), 2.64–2.79 (m, 3H), 3.14 (d, 1H, J=13), 3.21 (d, 1H, J=13), 3.78 (s 3H), 5.96 (s, 1H), 6.54 (d, 1H, J=2.6), 6.71 (d, 2H, J=7.1), 6.77 (dd, 1H, J=2.6, 8.7), 7.06–7.23 (m, 4H) ); $^{13}C$ NMR (100 MHz, $CDCl_3$) δ 30.71, 32.10, 34.62, 36.09, 43.62, 46.36, 55.20, 112.78, 112.84, 125.53, 126.68, 127.96, 128.12, 130.08, 133.01, 137.24, 137.28, 157.75, 169.16, 198.81; MS m/z 319 $(M+H)^+$. Anal. Calcd. for $C_{22}H_{22}O_2$: C, 82.99; H, 6.96; N, 0. Found: C, 83.21; H, 7.08; N, <0.10.

Preparation 4

2(3H)-Phenanthrenone, 4,4a,9,10-tetrahydro-7-hydroxy-4a-(phenylmethyl)-, (S)—

To a stirring solution of 40 g (0.126 mol) of the title product of Preparation 3 and 46.5 g (0.126 mol) of tetrabutylammonium iodide in 630 mL of dichloromethane at −78° C. under $N_2$ atmosphere was added 300 mL of 1 M boron trichloride in methylene chloride. The resultant solution was allowed to warm to RT for 1.5 h, then poured into excess ice and stirred rapidly, overnight. The mixture was extracted with dichloromethane, dried over $Na_2SO_4$, filtered, and concentrated to dryness. Purification by flash chromatography over $SiO_2$ using 20% EtOAc to 60% EtOAc in hexanes as the gradient eluant afforded 33.3 g of the title product of this preparation as an off-white powder (87%). $^1H$ NMR (400 MHz, $CD_3OD$) δ 1.81–2.00 (m, 2H), 2.26 (dt, 1H, J=4.2, 13), 2.40 (dd, 1H, J=4.5, 18), 2.53 (ddd, 1H, J=1.7, 5.6, 14), 2.58–2.80 (m, 3H), 3.20 (d, 1H, J=13), 3.26 (d, 1H, J=13), 5.92 (s, 1H), 6.45 (d, 1H, J=2.5), 6.67 (dd, 1H, J=2.5, 8.5), 6.76 (d, 2H, J=6.6), 7.05–7.14 (m, 4H); $^{13}C$ NMR (100 MHz, $CD_3OD$) δ 30.22, 32.03, 34.08, 36.04, 43.73, 45.97, 113.76, 113.91, 124.50, 126.25, 127.49, 127.94, 129.84, 131.86, 137.0, 137.71, 155.34, 171.73, 200.33; MS m/z 305 $(M+H)^+$.

Preferably, the title product of this preparation can be obtained by the following method: A solution of 9.45 g (0.02971 mol) of the title product of Preparation 3 and 6.65 g (0.04458 mol) of DL-methionine in 200 ml of methane sulfonic acid under nitrogen was stirred at room temperature. The resultant solution was allowed to stir overnight. Ice water was then poured into the mixture, and the precipitate was filtered. The filter cake was washed with water and taken into ethyl acetate. The organic layer was washed with NaHCO$_3$(sat), dried over Na$_2$SO$_4$ and concentrated to give 8 g of the title product of this preparation as an off-white powder (90%).

Preparation 5

2(1H)-Phenanthrenone, 3,4,4a,9,10,10a-hexahydro-7-hydroxy-4a-(phenylmethyl)-, (4aS-trans)-

Ammonia, (1.5 L) was condensed into a round bottom flask at −78° C. equipped with a dry ice reflux condenser at −78° C. and a mechanical stirrer. To this flask was added 0.7 g (99 mmol) of lithium wire and the solution turned dark blue. A solution of 10 g (32.8 mmol) of the title product of Preparation 4 in 400 mL of 1:1 dioxane:ether was added to the mixture slowly in order to keep the reaction a dark blue. As the blue color dissipated, a small amount of lithium wire was added to the mixture to regenerate the blue color. The total amount of lithium added to the reaction mixture did not exceed 3.5 g (495 mmol). After the complete addition of the title product of Preparation 4, the reaction was stirred an additional 30 min, then 14 g of solid ammonium chloride was added and immediate dissipation of the blue color was observed. H$_2$O was added to the mixture and it was extracted with EtOAc, dried over Na$_2$SO$_4$, filtered and concentrated to dryness. The crude product was purified by flash chromatography over SiO$_2$ using 15% EtOAc to 20% EtOAc in hexanes as the gradient eluant to afford 8.16 g of the title product as the major product of this preparation (white solid) (81%). A trace of the cis-product was also obtained. $^1$H NMR (400 MHz, CD$_3$OD) δ 1.52 (dt, 1H, J=4.5, 13), 1.64–1.71 (m, 1H), 1.90–2.15 (m, 2H), 2.27 (ddd, 1H, J=2.5, 3.7, 15), 2.39 (dm, 1H, J=15), 2.48 (ddd, 1H, J=2.0, 6.5, 13), 2.72 (t, 1H, J=14), 2.84 (d, 1H, J=13), 2.89–3.01 (m, 3H), 3.22 (d, 1H, J=13), 6.17 (d, 1H, J=8.5), 6.24 (dd, 1H, J=2.5,8.5), 6.53 (d, 1H, J=2.5), 6.65–6.68 (m, 1H), 7.04–7.13, (m, 3H); $^{13}$C NMR (100 MHz, CD$_3$OD) δ; 27.9, 33.7, 34.8, 36.0, 37.6, 39.4,43.6, 44.0, 111.3, 114.6, 125.7, 127.0, 127.9, 130.5, 133.4, 136.8, 138.0, 155.1, 212.7; MS m/z 307 (M+H)$^+$.

Preparation 6

1-(1(RS)-Benzyl-6-bromo-3,4-dihydro-1H-naphthalen-2-ylidene)-pyrrolidinium bromide A solution of the bisulfite adduct of bromotetralone of formula A-1 wherein R$_x$ is Br (250 g, 760 mmol) (commercially available) in saturated sodium bicarbonate (1.25 L) and ethyl acetate (2.5 L) was stirred vigorously overnight. Phases were separated and the organic phase was transferred to a new flask and toluene (1 L) was added. The solution was distilled under reduced pressure to a volume of about 500 mL. An additional 500 mL of toluene was added and distilled under reduced pressure to a volume of about 300 mL. The solution was cooled to room temperature and pyrrolidine (54.1 g, 760 mmol) was added. The reaction was heated to 150° C. under Dean-Stark conditions. After 2 hr, about 13 mL of water was collected and concentration of a small sample showed the reaction was complete by NMR. The toluene solution of pyrrolidine enamine was cooled to 90° C. and benzyl bromide (105 mL, 912 mmol) was added dropwise. After 30 min, solids began to granulate and the solution became very thick. An additional 500 mL of toluene was added to aid stirring and heating was continued at 90° C. for 2 h. The slurry was allowed to cool to room temperature and granulate overnight. The solids were filtered and washed with toluene (2×500 mL). After drying in a vacuum oven overnight (50° C.), the title product of this preparation as a brown solid was collected: 250 g (557 mmol), 73% yield; mp 203–205° C.; IR (film) v 1654, 1596 cm$^{-1}$; $^1$H NMR (CDCl$_3$) δ 7.25 (s, 1H), 7.17–7.13 (m, 3H), 7.08 (dd, 1H, J=8.3, 1.7 Hz), 6.98–6.93 (m, 2H), 6.68 (d, 1H, J=8.3 Hz), 4.29 (dd, 1H, J=7.5, 7.5 Hz), 4.25–4.17 (m, 2H), 3.95–3.86 (m, 1H), 3.62–3.49 (m, 2H), 3.27 (dd, 1H, J=13.7, 6.6 Hz), 3.14–3.05 (m, 3H), 2.07–1.95 (m, 3H), 1.92–1.84 (m, 1H); $^{13}$C NMR (CDCl$_3$) δ 189.2, 137.2, 136.1, 132.2, 131.2, 130.9, 130.6, 129.8, 129.2, 127.8, 122.1, 55.1, 55.2, 51.3, 39.3, 34.0, 25.6, 24.9, 24.2; Anal. calcd for C$_{21}$H$_{22}$BrN: C, 56.15; H, 5.16; N, 3.12. Found: C, 55.64; H, 5.22; N, 3.22.

Preparation 7

1(R)-Benzyl-5-bromo-9(S)-hydro-10(R)-hydroxy-10(R)-methyl-tricyclo[7.3.1.0$^{2,7}$]trideca-2,4,6-trien-13-one A solution of the title product of Preparation 6 (245 g, 545 mmol) in toluene (275 mL) and water (275 mL) was heated to 100° C. for 2 h and then cooled to room temperature. Phases were separated and the aqueous washed with toluene (250 mL). The combined organics and (S)-(−)-α-methylbenzylamine (71 mL, 545 mmol) were heated to 150° C. under Dean-Stark conditions. Once 250 mL of toluene and water were collected the reaction was allowed to cool to room temperature and stir overnight. The solution was then cooled to −10° C. and methyl vinyl ketone (50 mL, 600 mmol), freshly distilled from potassium carbonate under reduced pressure, was added dropwise over 15 min. Once addition was complete the reaction was stirred at −10° C. for 20 min and then allowed to warm to room temperature. The solution was heated to 38° C. and monitored by NMR. After 7 h no starting material was observed and the reaction was cooled to room temperature. Sulfuric acid (10%, 750 mL) was added and the solution was stirred overnight during which time solids precipitated out of solution. These solids were filtered and washed with water (500 mL) and isopropyl ether (1000 mL). After drying in a vacuum oven (45° C.) overnight, the title product of this preparation as a light brown solid was collected: 159 g (413 mmol), 76% yield; mp154–155° C.; IR (film) v3412, 1717 cm$^{-1}$; [α]$^{25}_D$ −48.75; $^1$H NMR (CDCl$_3$) δ 7.26–7.19 (m, 2H 7.13–7.08 (m, 2H), 7.06–7.00 (m, 4H), 3.72 (d, 1H, J=15.8 Hz), 3.35 (dd, 1H, J=18.0, 6.6 Hz), 3.12 (d, 2H, J=15.8 Hz), 3.11 (d, 1H, J=18.0 Hz), 2.66 (d, 1H, J=6.6 Hz), 2.28 (ddd, 1H, J=13.1, 13.1, 4.5 Hz), 2.06 (bs, 1H), 1.67 (ddd, 1H, J=13.1, 4.5, 2.7 Hz), 1.57–1.50 (m,1H), 1.44–1.38 (m, 1H), 1.36 (s, 3H); $^{13}$C NMR (CDCl$_3$) δ 212.9, 139.6, 138.4, 136.8, 130.5, 130.4, 130.4, 128.7, 128.1, 125.8, 120.6, 79.3, 58.4, 54.2, 41.9, 38.5, 34.0, 32.9, 28.1; Anal. Calcd for C$_{21}$H$_{21}$BrO$_2$: C, 65.46; H, 5.49. Found: C, 65.42, H, 5.44; the structure and absolute configuration were confirmed by single crystal X-ray analysis.

Preparation 8

4a(S)-Benzyl-7-bromo-2-ethoxy-3,4,4a,9-tetrahydro-phenanthrene

Sodium methoxide (8.4 g, 156 mmol) was added slowly to a solution of the title product of Preparation 7 (60 g, 156 mmol) in 2B ethanol (540 mL) and stirred for 4 h at 80° C. HPLC (Symmetry $C_8$ 150 mm column, 70% $CH_3CN$ 30% water, 1 mL/min; $4_T$ 3.2 min, $11_T$ 5.1 min) showed starting material was consumed and the reaction was cooled to −10° C. Acetylchloride (33 mL, 467 mmol) as a solution in 2B ethanol (180 mL) was also cooled to −10° C. The reaction mixture was added slowly to the acetyl chloride solution such that the temperature remained at about 0° C. Once addition was complete the resulting solids were allowed to granulate for 1 h at 0° C. The solids were filtered and washed with 2B ethanol (2×100 mL) and placed in a vacuum oven at room temperature overnight. The resulting solids contained 7.59% NaCl ash and could be taken on without purification. After drying in a vacuum oven overnight (room temperature), the title product of this preparation as a pale yellow solid was collected: 56.1 g (131 mmol), 84% yield; mp 134–135° C; IR (film) v1656, 1631 $cm^{-1}$; $[\alpha]^{25}_D$ +170.68; $^1H$ NMR (acetone-$d_6$) δ 7.37–7.32 (m, 2H), 7.11–7.05 (m, 2H), 7.01–6.95 (m, 2H), 6.53 (d, 2H, J=7.1 Hz), 5.49 (dd, 1H, J=5.8, 2.5 Hz), 5.47 (d, 1H, J=1.2 Hz), 3.91 (q, 2H, J=7.1 Hz), 3.03 (d, 1H, J=12.5 Hz), 2.91 (dd, 1H, J=21.6, 5.8 Hz), 2.77–2.69 (m, 1H), 2.68 (d, 1H, J=12.5 Hz), 2.59 (dd, 1H, J=12.9, 6.0 Hz), 2.27 (dd, 1H, J=17.1, 6.0 Hz), 2.13 (d, 1H, J=21.6 Hz), 1.79 (ddd, 1H, J=12.9, 12.9, 5.8 Hz), 1.32 (t, 3H, J=7.1 Hz); $^{13}C$ NMR (acetone-$d_6$) δ 155.2, 141.1, 140.1, 137.8, 136.2, 130.7, 129.9, 128.8, 127.9, 127.1, 126.0, 119.3, 118.7, 98.9, 62.5, 44.3, 41.9, 32.4, 30.0, 25.6, 14.3;

Anal. Calcd for $C_{23}H_{23}BrO$: C, 69.88; H, 5.86. Found: C, 70.20; H, 5.84.

Preparation 9

4a(S)-Benzyl-7-hydroxy-2-ethoxy-3,4,4a,9-tetrahydro-phenanthrene

To a solution of the title product of Preparation 8 (3.69 g, 9.30 mmol) in THF (46 ml) at −78° C. under nitrogen was added n-BuLi (2.7 m sol. in heptane) (3.79 ml, 10.23 mmol, 1.1 eq). The dark red mixture was treated with $B(OiPr)_3$ (2.78 ml, 12.09 mmol, 1.3 eq, fresh distilled over Na prior to use). The reaction mixture was warmed to −25° C. over 3 hr. The orange mixture was added to 3M NaOH (1.3 eq) over 10 min. After 10 min $H_2O_2$ (30%, 1.3 eq) was added and stirring was continued for 2 hr. Quenched with half sat. $NH_4Cl$ (40 ml) and diluted with toluene (70 ml), the organic layer was separated and washed with 1% sodium sulfite solution to remove peroxides. The organic phase was separated and concentrated. The crude mixture was purified with $SiO_2$ column chromatography with 50% ethyl acetate in hexane as elutant to obtain 2.78 g of the title compound of this preparation (90%), M/Z =333 $(M+H)^+$.

Preparation 10

2,7-Phenanthrenediol, 1,2,3,4,4a,9,10,10a-octahydro-4a-(phenylmethyl)-2-(1-propynyl)-, [2R-(2α,4aα,10aβ)]- and 2,7-Phenanthrenediol, 1,2,3,4,4a,9,10,10a-octahydro-4a-(phenylmethyl)-2-(1-propynyl)-, [2S-(2α,4aβ,10aα)]-

To a stirring solution of 183 mL of THF saturated with propyne gas at 0° C. was added 143 mL of 1 M lithium diisopropylamide in THF and the resultant mixture stirred under nitrogen atmosphere for 20 min. A solution of 7.3 g (23.8 mmol) of the title product of Preparation 5 in 250 mL of THF was added dropwise, and the reaction mixture was warmed to RT and stirred overnight. Saturated, aqueous ammonium chloride was added, and the mixture was extracted with EtOAc, dried over $Na_2SO_4$, filtered, and concentrated to dryness. Purification by flash chromatography over $SiO_2$ using 2% acetone in dichloromethane to 4% acetone as the eluant afforded 4.0 g (49%) of the first title product of this preparation (higher Rf) and 2.4 g (29%) of the second title product of this preparation as white solids.

Physical characteristics of the first title product of this example are as follows: mp 227–229° C. (decomp.), $^1H$ NMR (400 MHz, $CD_3OD$) δ 1.42 (mt, 1H, J=14), 1.61.(ddd, 1H, J=3.4, 4.1, 8.8), 1.72 (s, 3H), 1.73–1.82 (m, 2H), 1.84–2.10 (m, 5H), 2.55 (d, 1H, J=13), 2.83–2.93 (m) and 2.94 (d, 3H, J=13), 6.10 (d, 1H, J=8.3), 6.23 (dd, 1H, J=2.5, 8.4), 6.52–6.55 (m, 3H), 7.00–7.05 (m, 3H); $^{13}C$ NMR (62 MHz, $CD_3OD$) δ 2.5, 24.1, 27.3, 30.5, 35.8, 36.1, 39.1, 40.2, 42.4, 68.9, 79.5, 82.3, 110.9, 114.7, 125.4, 126.8, 127.5, 130.7, 135.1, 136.9, 138.3, 154.8; MS m/z 346 $(M+H)^+$, 329 $(M-OH)^+$.

Physical characteristics of the second title product of this example are as follows: mp 222–223° C. (decomp.); $^1H$ NMR (400 MHz, $CD_3OD$) δ 1.46 (mt, 1H, J=14), 1.54–1.60. (m, 1H), 1.83 (s) overlap with 1.75–1.94 (m, 8H), 2.08 (mt, 1H, J=13), 2.20 (dt, 1H, J=4, 14), 2.57 (d, 1H, J=13), 2.88 (t, 2H, J=8.7), 2.94 (d, 1H, J=13), 6.08 (d, 1H, J=8.3), 6.20 (dd, 1H, J=2.4, 8.3), 6.50 (d, 1H, J=2.4), 6.53–6.56 (m, 2H), 7.01–7.06 (m, 3H); $^{13}C$ NMR (62 MHz, $CD_3OD$) δ 1.7, 24.1, 27.4, 27.6, 35.0, 35.2, 36.4, 39.0, 41.6, 65.5, 76.9, 84.5, 110.8, 114.6, 125.3, 126.8, 127.4, 130.7, 135.0, 136.9, 138.4, 154.7; MS m/z 346 $(M+H)^+$, 329 $(M-OH)^+$.

Preparation 11

2,7-Phenanthrenediol, 1,2,3,4,4a,9,10,10a-octahydro-4a-(phenylmethyl)-2-propyl-[2R-(2α,4aα,10aβ)]-

A mixture of 975 mg of the first title product of Preparation 10, 195 mg of 10% Pd/C, and 100 mg $K_2CO_3$ in MeOH was shaken under 40 p.s.i. $H_2$ for 16 h. The mixture was filtered through Celite® and concentrated to afford 450 mg of the title product of this preparation as a white solid. MS: 368 $(M+18)^+$.

Preparation 12

2,7-Phenanthrenediol, 1,2,3,4,4a,9,10,10a-octahydro-4a-(phenylmethyl)-2-vinyl-[2R-(2α,4aα,10aβ)]-

To a stirring solution of 25 mL of THF and 1 g of 2(1H)-phenanthrenone, 3,4,4a,9,10,10a-hexahydro-7-hydroxy-4a-(phenylmethyl)-, (4aS-trans)-, prepared by procedures described in Preparation 5, was added 9.8 ml of 1M vinyl magnesium bromide at 0° C. The resultant solution was allowed to warm up to room temperature at its own accord overnight. Saturated, aqueous ammonium chloride was added, and the mixture was extracted with EtOAc, dried over $Na_2SO_4$, filtered, and concentrated to dryness. Purification by flash chromatography over $SiO_2$ using 2% acetone in dichloromethane to 4% acetone in dichloromethane as the eluant afforded 420 mg (38%) of the title product of this preparation. MS m/z 317 $(M-17)^+$.

Preparation 13

2,7-Phenanthrenediol, 1,2,3,4,4a,9,10,10a-octahydro-4a-(phenylmethyl)-2-ethyl-[2R-(2α,4aα,10aβ)]-

A mixture of 420 mg of the title product of Preparation 12, 210 mg of 10% Pd/C, in EtOH was shaken under 40 p.s.i. $H_2$ for 20 min. The mixture was filtered through Celite® and concentrated to afford 400 mg of the title product of this preparation as a white solid. MS: 319 (M–OH)$^+$.

Preparation 14

Spiro[oxirane-2,2'(1'H)-phenanthren]-7'-ol, 3',4',4'a, 9',10',10'a-hexahydro-4'a-(phenylmethyl)-, [2'R-(2'α, 4'aα, 10'aβ)]-

A solution of 91 mg of trimethyl sulfonium iodide in 1 mL of anhydrous DMF was added 55 mg of t-BuOK at 0° C. under N$_2$ atmosphere and stirred for 5 min. To the resultant solution was added 20 mg of 2(1H)-phenanthrenone, 3,4, 4a,9,10,10a-hexahydro-7-hydroxy-4a-(phenylmethyl)-, (4aS-trans)-, prepared by procedures described in Preparation 5, in 1 mL of DMF slowly and stirred for another 1 h at 0° C. The reaction was quenched with NH$_4$Cl (sat), extracted with EtOAc (×3), washed with brine, dried over Na$_2$SO$_4$, filtered and concentrated to dryness. Purification by flash chromatography SiO$_2$ using 100% CH$_2$Cl$_2$ to 2% acetone in CH$_2$Cl$_2$ as the gradient eluant afforded 13 mg (70%) of the title product of this preparation as white fluffy powder. MS m/z 303 (M–17)$^+$.

Preparation 15

2,7-Phenanthrenediol, 1,2,3,4,4a,9,10,10a-octahydro-2-(ethoxymethyl)-4a-(phenylmethyl)-, [2R-(2α,4aα,10aβ)]-

A solution of 20 mg of spiro[oxirane-2,2'(1'H)-phenanthren]-7'-ol, 3',4',4'a,9',10',10'a-hexahydro-4'a-(phenylmethyl)-, [2'R-(2'α,4'aα, 10'aβ)]-, prepared by procedures described in Preparation 14, and 10 mg of sodium ethoxide in 5 ml of EtOH was heated to reflux for 3 h. The reaction was cooled and quenched with NH$_4$Cl(sat), extracted with EtOAc (×3), washed with brine, dried over Na$_2$SO$_4$, filtered and concentrated to dryness. Purification by prep. TLC SiO$_2$ using 30% EtOAc in hexane as the eluant afforded 20 mg (88%) of the title product of this preparation as white fluffy powder. MS m/z 356 (M–17)$^+$.

Preparation 16

2,7-Phenanthrenediol, 1,2,3,4,4a,9,10,10a-octahydro-4a-(phenylmethyl)-2-methyl-[2R-(2α, 4aα, 10aβ)]-

To a stirring solution of 200 ml of THF and 6.8 g of spiro[oxirane-2,2'(1'H)-phenanthren]-7'-ol, 3',4',4'a,9',10', 10'a-hexahydro-4'a-(phenylmethyl)-, [2'R-(2'α,4'aα, 10'aβ)]-, prepared by procedures described in Preparation 14, was added slowly 64 ml of 1M LAH/THF at 0° C. under nitrogen. The resultant solution was allowed to stir at 0° C. for 1 hr. EtOAc was added to quench the excess hydride and then saturated, aqueous ammonium chloride was added, and the mixture was extracted with EtOAc, dried over Na$_2$SO$_4$, filtered and concentrated to dryness. Purification by flash chromatography over SiO$_2$ using 25% ethyl acetate in hexane as the eluant afforded 4.9 g (72%) of the title product of this preparation. MS m/z 305 (M–17)$^+$.

Preparation 17

2,7-Phenanthrenediol, 1,2,3,4,4a,9,10,10a-octahydro-4a-(phenylmethyl)-2-(trifluoromethyl)-, (2R,4aS,10aR)-

To a solution of 455 mg of 2(1H)-phenanthrenone, 3,4, 4a,9,10,10a-hexahydro-7-hydroxy-4a-(phenylmethyl)-, (4aS-trans)-, prepared by procedures described in Preparation 5, in 20 mL of anhydrous THF and 15 mL of 1M trifluoromethyl trimethylsilane was added 194 mg of t-butylammoniumfluoride (TBAF) at 0° C. under nitrogen atmosphere for 10 min. The mixture was then stirred at rt for 3 hr. Two additional equivalents of TBAF were added and stirred for 1 hr at rt to hydrolyze the trimethylsilane ether. The mixture was concentrated and purified by flash chromatography SiO$_2$ using 100% hexane to 20% ethyl acetate in hexane as the gradient elutant afforded 518 mg (93%) of the title product of this preparation as white fluffy powder. MS m/z 375 (M–1)$^+$.

Alternatively, to a solution of 25 g of 2(1H)-phenanthrenone, 3,4,4a,9,10,10a-hexahydro-7-hydroxy-4a-(phenylmethyl)-, (4aS-trans)-, prepared by procedures described in Preparation 5, in 375 mL of anhydrous THF and 60 mL of trifluoromethyl trimethylsilane was added 1.5 g of CsF at 0° C. under nitrogen atmosphere for 10 min. The mixture was then stirred at rt for 3 hr. Hydrogen chloride 1 N solution (250 mL) was added and stirred overnight at rt to hydrolyze the trimethylsilane ether. The mixture was concentrated and purified by crystallization using methylene chloride and hexane to yield 24.4 g (80%) of the title product of this preparation as white fluffy powder. MS m/z 375 (M–1)$^+$.

Preparation 18

Acetonitrile, [[4b,5,6,7,8,8a,9,10-octahydro-7-hydroxy-4b-(phenylmethyl)-7-(trifluoromethyl)-2-phenanthrenyl]oxy]-, [4bS-(4bα,7α,8aβ)]-

To a solution of 500 mg of the title product of Preparation 17 and 58 mg of 60% NaH in 20 ml of anhydrous CH$_3$CN was added 0.46 ml bromoacetonitrile under N$_2$ atmosphere. The reaction was heated to 85° C. overnight. The reaction was quenched with NH$_4$Cl(sat), extracted with EtOAc (×3), washed with brine, dried over Na$_2$SO$_4$, filtered and concentrated to dryness. Purification by flash chromatography SiO$_2$ using 8% ethyl acetate in toluene as the eluant afforded 500 mg (90%) of the title product of this preparation as white fluffy powder. MS m/z 416 (M+H)$^+$.

Preparation 19

Ethanimidamide, N-hydroxy-2-[[4b,5,6,7,8,8a,9,10-octahydro-7-hydroxy-4b-(phenylmethyl)-7-(trifluoromethyl)-2-phenanthrenyl]oxy]-, [4bS-(4bα, 7α,8aβ)]-

To a solution of 260 mg of the title product of Preparation 18 and 173 mg of K$_2$CO$_3$ in 10 mL of anhydrous EtOH was added 65 mg of NH$_2$OH.HCl and heated to reflux for 6 h. The reaction was then concentrated to dryness and purified by prep. TLC using 3% MeOH in CH$_2$Cl$_2$ as the eluant to yield 131 mg of the title product of this preparation as white powder (50%). MS m/z 419 (M+H)$^+$.

Example 1

2-Phenanthrenol, 7-[[5-[(dimethylamino)methyl]-1, 2,4-oxadiazol-3-yl]methoxy]-1,2,3,4,4a,9,10,10a-octahydro-4a-(phenylmethyl)-2-(trifluoromethyl)-, [2R-(2α,4aα, 10aβ)]-

A solution of 32.5 mg of the title product of Preparation 19 and 3.2 mg of 60% NaH in 2 mL of anhydrous THF was heated to 60° C. for 20 min. The solution was cooled to RT and 0.020 mL of ethyl-N, N-dimethyl glycine was added to the solution. The resultant mixture was heated to reflux for 1 h then cooled to rt, filtered and concentrated to dryness. Purification by preparative TLC using 8% methanol in CH$_2$Cl$_2$ and few drops of NH$_4$OH as the eluant yielded 21.2 mg of the title product of this example (57%). MS m/z 516 (M+H)$^+$.

Example 2 to Example 22

Using procedures analogous to those described above, particularly in Preparations 17 to 19 and Example 1, the following compounds of the present invention were prepared from the corresponding phenol, e.g., the compound of formula C-3 in Scheme C above:

Example 2  2-Phenanthrenol, 1,2,3,4,4a,9,10,10a-octahydro-7-[[5-[2-(4-morpholinyl)ethyl]-1,2,4-oxadiazol-3-yl]methoxy]-4a-(phenylmethyl)-2-(trifluoromethyl)-, (2R,4aS,10aR)-
Mass: M + 1 = 572.4.

Example 3  2-Phenanthrenol, 1,2,3,4, 4a,9,10,10a-octahydro-4a-(phenylmethyl)-7-[[5-(1-piperidinylmethyl)-1,2,4-oxadiazol-3-yl]methoxy]-2-(trifluoromethyl)-, (2R,4aS,10aR)-
Mass: M + 1 = 556.4.

Example 4  2-Phenanthrenol, 1,2,3,4 ,4a,9,10,10a-octahydro-4a-(phenylmethyl)-7-[[5-[2-(1-piperidinyl)ethyl]-1,2,4-oxadiazol-3-yl]methoxy]-2-(1-propynyl)-, (2R,4aS,10aR)-
Mass: M + 1 = 540.5.

Example 5  2-Phenanthrenol, 1,2,3,4,4a,9,10,10a-octahydro-4a-(phenylmethyl)-2-(1-propynyl)-7-[[5-(1,2,5,6-tetrahydro-1-methyl-3-pyridinyl)-1,2,4-oxadiazol-3-yl]methoxy]-, (2R,4aS,10aR)-
Mass: M + 1 = 524.4.

Example 6  2-Phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-propyl-, (2R,4aS,10aR)-
Mass: M + 1 = 516.2.

Example 7  2-Phenanthrenol,1,2,3,4,4a,9,10,10a-octahydro-7-[[5-(1-methyl-3-piperidinyl)-1,2,4-oxadiazol-3-yl]methoxyl-4a-(phenylmethyl)-2-propyl-, (2R,4aS,10aR)-
Mass: M + 1 = 530.3.

Example 8  2-Phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxy]-2-propyl-, (2R,4aS,10aR)-
Mass: M + 1 = 544.3.

Example 9  2-Phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-propyl-, (2R,4aS,10aR)-
Mass: M + 1 = 504.3.

Example 10  2-Phenanthrenol, 1,2,3,4,4a,9,10,10a-octahydro-4a-(phenylmethyl)-7-[[5-(1-piperidinylmethyl)-1,2,4-oxadiazol-3-yl]methoxy]-2-propyl-, (2R,4aS,10aR)-
Mass: M + 1 = 530.3.

Example 11  2-Phenanthrenol, 7-[[5-[2-(1-azetidinyl)ethyl]-1,2,4-oxadiazol-3-yl]methoxyll-1,2,3,4,4a,9,10,10a-octahydro-4a-(phenyl methyl)-2-(trifluoromethyl)-, (2R,4aS,10aR)-
Mass: M + 1 = 542.4.

Example 12  2-Phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-(trifluoromethyl)-, (2R,4aS,10aR)-
Mass: M + 1 = 556.4.

Example 13  2-Phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxyl-2-(trifluoromethyl)-, (2R,4aS,10aR)-
Mass: M + 1 = 570.4.

Example 14  2-Phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-
Mass: M + 1 = 530.4.

Example 15  2-Phenanthrenol, 7-[f5-[2-(1-azetidinyl)ethyl]-1,2,4-oxadiazol-3-yl]methoxy]-1,2,3,4,4a,9,10,10a-octahydro-4a-(phenylmethyl)-2-(1-propynyl)-, (2R,4aS,10aR)-
Mass: M + 1 = 512.4.

Example 16  2-Phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-(1-propynyl)-, (2R,4aS,10aR)-
Mass: M + 1 = 526.4.

Example 17  2-Phenanthrenol, 7-[[5-[2-(diethylamino)ethyl]-1,2,4-oxadiazol-3-yl]methoxy]-1,2,3,4,4a,9,10,10a-octahydro-4a-(phenylmethyl )-2-(trifluoromethyl)-, (2R,4aS,10aR)-
Mass: M + 1 = 558.4.

Example 18  2-Phenanthrenal, 7-[[5-methyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-
Mass: M + 1 = 473.5.

Example 19  Phenanthren-2-ol, 7-(5-dimethylaminomethyl-[1,2,4]oxadiazol-3-ylmethoxy)-4a-ethyl-2-prop-1-ynyl-1,2,3,4,4a,9,10,10a-octahydro-, (2R,4aR,10aR)-
Mass: M + 1 = 424.

Example 20  Phenanthren-2-ol, 7-[5-(2-dimethylaminoethyl)-[1,2,4]oxadiazol-3-ylmethoxy]-4a-ethyl-2-prop-1-ynyl-1,2,3,4,4a,9,10,10a-octahydro-, (2R,4aR,10aR)-
Mass: M + 1 = 438.

Example 21  Phenanthren-2-ol, 4a-ethyl-7-[5-(2-morpholin-4-yl-ethyl)-[1,2,4]oxadiazol-3-ylmethoxy]-2-prop-1-ynyl-1,2,3,4,4a,9,10,10a-octahydro-,(2R,4aR,10aR)-
Mass: M + 1 = 480.

Example 22  Phenanthren-2-ol, 4a-ethyl-7-(5-piperidin-1-ylmethyl-[1,2,4]oxadiazol-3-ylmethoxy)-2-prop-1-ynyl-1,2,3,4,4a,9,10,10a-octahydro-, (2R,4aR,10aR)-
Mass: M + 1 = 464.

What is claimed is:
1. A compound of Formula I

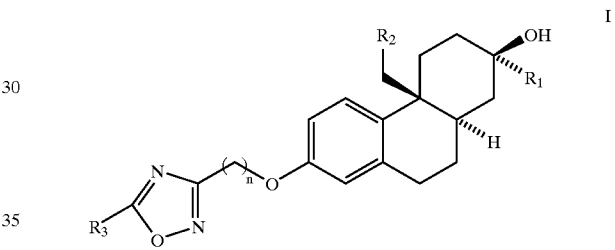

a prodrug of said compound or a pharmaceutically acceptable salt of said compound or prodrug;
wherein R$_1$ is a) —(C$_1$–C$_6$)alkyl optionally substituted with —CF$_3$, b) —C≡C—CH$_3$, c) —C≡C—Cl, d) —C≡C—CF$_3$, e) —CH$_2$O(C$_1$–C$_4$)alkyl optionally substituted with —CF$_3$ or f) —CF$_3$;
R$_2$ is a) —(C$_1$–C$_5$)alkyl, b) —(C$_2$–C$_5$)alkenyl or c)-phenyl optionally substituted with one of the following: —OH, —NR$_8$R$_9$, —NR$_8$—C(O)—(C$_1$–C$_4$)alkyl, —CN, —Z-het, —O—(C$_1$–C$_3$)alkyl-C(O)—NR$_8$R$_9$, —NR$_8$—Z—C(O)—NR$_8$R$_9$, —Z—NR$_8$—SO$_2$—R$_9$, —NR$_8$—SO$_2$-het, —O—C(O)—(C$_1$–C$_4$)alkyl or —O—SO$_2$—(C$_1$–C$_4$)alkyl;
Z for each occurrence is independently —(C$_0$–C$_4$)alkyl;
R$_3$ is a) —(C$_1$–C$_6$)alkyl, b) —Z—NR$_4$R$_5$ or c) —Z-het;
R$_4$ and R$_5$ are each independently a) hydrogen or b) —(C$_1$–C$_3$)alkyl;
het is an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring; and optionally substituted with one to three R$_6$;
R$_6$ is a) —(C$_1$–C$_6$)alkyl optionally substituted with one to three R$_7$, b) —Z—NR$_8$R$_9$ or c) —Z—C(O)—NR$_8$R$_9$;
R$_7$ for each occurrence is independently a) halo, b) —OH, c) oxo or d) —O(C$_1$–C$_6$)alkyl;

$R_8$ and $R_9$ for each occurrence are independently a) —H or b) —($C_1$–$C_3$)alkyl;

or $R_8$ and $R_9$ are taken together with N to form het;

n is one to three;

provided that:

1) when $R_1$ is —C≡C—$CH_3$, $R_2$ is phenyl and n is one, then $R_3$ is other than —$CH_2$—N($CH_3$)$_2$, —($CH_2$)$_2$—N($CH_3$)$_2$, —$CH_2$-piperidinyl or —($CH_2$)$_2$-morpholinyl;
2) when $R_1$ is —($CH_2$)$_2$—$CH_3$, $R_2$ is phenyl and n is one, then $R_3$ is other than -t-butyl or -3,5-dimethyl-4-isoxazolyl.

2. A compound of claim 1 of Formula II

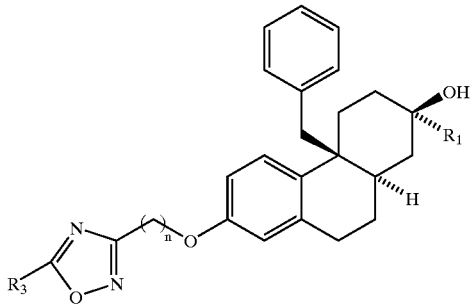

II a prodrug of said compound or a pharmaceutically acceptable salt of said compound or prodrug;

wherein $R_1$ is a) —($C_1$–$C_6$)alkyl optionally substituted with —$CF_3$, b) —C≡C—$CH_3$, c) —$CF_3$ or d) —$CH_2$O($C_2$–$C_4$)alkyl; and n is one or two.

3. A compound of claim 2 wherein $R_1$ is a) —$CH_2CH_2CH_3$, b) —C≡C—$CH_3$ or c) —$CF_3$; and n is one.

4. A compound of claim 3 wherein $R_1$ is a) —$CH_2CH_2CH_3$ or b) $CF_3$.

5. A compound of claim 4 wherein $R_3$ is —($C_1$–$C_2$)alkyl-$NR_4R_5$;

$R_4$ and $R_5$ are each independently a) methyl, b) ethyl, c) propyl or d) isopropyl.

6. A compound of claim 5 wherein $R_3$ is —($C_1$–$C_2$)alkyl-$NR_4R_5$;

$R_4$ and $R_5$ are each independently a) methyl or b) ethyl.

7. A compound of claim 3 wherein $R_3$ is —($C_0$–$C_2$)alkyl-het;

het is a) morpholinyl, b) pyrrolidinyl, c) piperidinyl, d) piperazinyl, e) hexahydro-azepinyl, f) azabicyclo[2.2.2]oct-3-yl, g) azabicyclo[3.2.1]oct-3-yl, h) 3,6-diazabicyclo[3.1.1]heptyl, i) 2,5-diazabicyclo[2.2.1]heptyl, j) 1,2,5,6-tetrahydro-pyridinyl, k) azetidinyl, l) 1,4-diazabicyclo[3.2.2]nonanyl, m) 3,6-diazabicyclo[3.2.2]nonanyl, n) octahydro-pyrido[1,2-a]pyrazinyl or o) hexahydro-1,4-diazepinyl;

the above het groups are optionally substituted with one or two $R_6$;

$R_6$ for each occurrence is independently a) methyl, b) ethyl or c) —$NR_8R_9$;

$R_8$ and $R_9$ for each occurrence are independently methyl or ethyl.

8. A compound of claim 7 wherein $R_3$ is —($C_0$–$C_2$)alkyl-het;

het is a) morpholinyl, b) piperidinyl, c) 1,2,5,6-tetrahydro-pyridinyl, d) azetidinyl or e) pyrrolidinyl;

the above het groups are optionally substituted with one or two $R_6$;

$R_6$ for each occurrence is independently a) methyl or b) ethyl.

9. A compound of claim 1 wherein $R_1$ is a) —$CH_2CH_2CH_3$, b) —C≡C—$CH_3$ or c) —$CF_3$;

$R_2$ is a) methyl, b) ethyl, c) propyl, d) ethenyl or e) propenyl;

$R_3$ is —($C_1$–$C_2$)alkyl-$NR_4R_5$;

$R_4$ and $R_5$ are each independently a) methyl or b) ethyl;

n is one.

10. A compound of claim 1 wherein $R_1$ is a) —$CH_2CH_2CH_3$, b) —C≡C—$CH_3$ or c) —$CF_3$;

$R_2$ is a) methyl, b) ethyl, c) propyl, d) ethenyl or e) propenyl;

$R_3$ is —($C_0$–$C_2$)alkyl-het;

het is a) morpholinyl, b) piperidinyl or c) pyrrolidinyl;

the above het groups are optionally substituted with one or two $R_6$;

$R_6$ for each occurrence is independently a) methyl or b) ethyl; and n is one.

11. A compound of claim 6 selected from the group consisting of:

2-phenanthrenol, 7-[[5-[(dimethylamino)methyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-;

2-phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-propyl-, (2R,4aS,10aR)-;

2-phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-; and 2-phenanthrenol, 7-[[5-[2-(diethylamino)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-.

12. A compound of claim 8 selected from the group consisting of:

2-phenanthrenol, 1,2,3,4,4a,9,10,10a-octahydro-7-[[5-[2-(4-morpholinyl)ethyl]-1,2,4-oxadiazol-3-yl]methoxy]-4a-(phenylmethyl)-2-(trifluoromethyl)-, (2R,4aS,10aR)-;

2-phenanthrenol, 1,2,3,4,4a,9,10,10a-octahydro-4a-(phenylmethyl)-7-[[5-(1-piperidinylmethyl)-1,2,4-oxadiazol-3-yl]methoxy]-2-(trifluoromethyl)-, (2R,4aS,10aR)-;

2-phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxy]-2-(1-propynyl)-, (2R,4aS,10aR)-;

2-phenanthrenol, 1,2,3,4,4a,9,10,10a-octahydro-4a-(phenylmethyl)-2-(1-propynyl)-7-[[5-(1,2,5,6-tetrahydro-1-methyl-3-pyridinyl)-1,2,4-oxadiazol-3-yl]methoxy]-, (2R,4aS,10aR)-;

2-phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-propyl-, (2R,4aS,10aR)-;

2-phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-propyl-, (2R,4aS,10aR)-;

2-phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxy]-2-propyl-, (2R,4aS,10aR)-;

2-phenanthrenol, 1,2,3,4,4a,9,10,10a-octahydro-4a-(phenylmethyl)-7-[[5-(1-piperidinylmethyl)-1,2,4-oxadiazol-3-yl]methoxy]-2-propyl-, (2R,4aS,10aR)-;

2-phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-;

2-phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-(trifluoromethyl)-, (2R,4aS,10aR)-;

2-phenanthrenol, 1,2,3,4,4a,9,10,10a-octahydro-4a-(phenylmethyl)-7-[[5-[2-(1-piperidinyl)ethyl]-1,2,4-oxadiazol-3-yl]methoxyl-2-(trifluoromethyl)-, (2R,4aS, 10aR)-;

2-phenanthrenol, 7-[[5-[2-(1-azetidinyl)ethyl]-1,2,4-oxadiazol-3-yl]methoxy]-1,2,3,4,4a,9,10,10a-octahydro-4a-(phenylmethyl)-2-(1-propynyl)-, (2R,4aS,10aR)-; and 2-phenanthrenol, 1,2,3,4,4a,9,10,10a-octahydro-7-[[5-(1-methyl-3-piperidinyl)-1,2,4-oxadiazol-3-yl]methoxy]-4a-(phenylmethyl)-2-(1-propynyl)-, (2R,4aS,10aR)-.

13. 2-Phenanthrenol, 7-[[5-methyl]-1,2,4-oxadiazol-3-yl]methoxy]-1,2,3,4,4a,9,10,10a-octahydro-4a-(phenylmethyl)-2-(trifluoromethyl)-, (2R,4aS,10aR)-, a compound of claim 4.

14. A compound of claim 9 selected from the group consisting of:

phenanthren-2-ol, 7-(5-dimethylaminomethyl-[1,2,4]oxadiazol-3-ylmethoxy)-4a-ethyl-2-prop-1-ynyl-1,2,3,4,4a,9,10,10a-octahydro-, (2R,4aR,10aR)-; and phenanthren-2-ol, 7-[5-(2-dimethylaminoethyl)-[1,2,4]oxadiazol-3-ylmethoxy]-4a-ethyl-2-prop-1-ynyl-1,2,3,4,4a,9,10,10a-octahydro-, (2R,4aR,10aR)-.

15. A compound of claim 10 selected from the group consisting of:

phenanthren-2-ol, 4a-ethyl-7-[5-(2-morpholin-4-yl-ethyl)-[1,2,4]oxadiazol-3-ylmethoxy]-2-prop-1-ynyl-1,2,3,4,4a,9,10,10a-octahydro-,(2R,4aR,10aR)-; and phenanthren-2-ol, 4a-ethyl-7-(5-piperidin-1-ylmethyl-[1,2,4]oxadiazol-3-ylmethoxy)-2-prop-1-ynyl-1,2,3,4,4a,9,10,10a-octahydro-,(2R,4aR,10aR)-.

16. A method for the treatment of a disease or condition selected from the group consisting of obesity, diabetes, depression, anxiety, neurodegeneration and inflammatory disease in a mammal, which comprises administering to the mammal a therapeutically effective amount of a compound of claim 1, a prodrug of said compound or a pharmaceutically acceptable salt of said compound or prodrug.

17. The method of claim 16 wherein the disease or condition is selected from the group consisting of obesity, diabetes, depression, anxiety and neurodegeneration.

18. The method of claim 17 wherein the condition is obesity.

19. The method of claim 18 which further comprises administering a $\beta_3$ agonist, a thyromimetic agent, an eating behavior modifying agent or a NPY antagonist.

20. The method of claim 19 wherein the eating behavior modifying agent is orlistat or sibutramine.

21. The method of claim 17 wherein the disease is diabetes.

22. The method of claim 21 which further comprises administering an aldose reductase inhibitor, a glycogen phosphorylase inhibitor, a sorbitol dehydrogenase inhibitor, insulin, a sulfonylurea, glipizide, glyburide, or chlorpropamide.

23. The method of claim 16 wherein the disease is a inflammatory disease.

24. A pharmaceutical composition comprising a therapeutically effective amount of a compound of claim 1, a prodrug of said compound or a pharmaceutically acceptable salt of said compound or prodrug; and a pharmaceutically acceptable carrier, vehicle or diluent.

25. A pharmaceutical combination composition comprising: a therapeutically effective amount of a composition comprising:

a first compound, said first compound being a compound of claim 1, a prodrug of said compound or a pharmaceutically acceptable salt of said compound or prodrug; and a second compound, said second compound being a $\beta_3$ agonist, a thyromimetic agent, an eating behavior modifying agent or a NPY antagonist.

26. A kit comprising:

a) a first compound, said first compound being a compound of claim 1, a prodrug of said compound or a pharmaceutically acceptable salt of said compound or prodrug and a pharmaceutically acceptable carrier, vehicle or diluent in a first unit dosage form;

b) a second compound, said second compound being a $\beta_3$ agonist, a thyromimetic agent, an eating behavior modifying agent or a NPY antagonist; and a pharmaceutically acceptable carrier, vehicle or diluent in a second unit dosage form; and c) a container for containing said first and second dosage forms; wherein the amounts of said first and second compounds result in a therapeutic effect.

27. A method for inducing weight loss in a mammal which comprises administering to the mammal a therapeutically effective amount of a compound of claim 1, a prodrug of said compound a pharmaceutically acceptable salt of said compound or prodrug.

28. A pharmaceutical combination composition comprising: a therapeutically effective amount of a composition comprising:

a first compound, said first compound being a compound of claim 1, a prodrug of said compound or a pharmaceutically acceptable salt of said compound or prodrug; and a second compound, said second compound being an aldose reductase inhibitor, a glycogen phosphorylase inhibitor, a sorbitol dehydrogenase inhibitor, insulin, a sulfonylureas, glipizide, glyburide, or chlorpropamide.

29. A method for the treatment of an inflammatory disease in a mammal which comprises administering to said mammal a therapeutically effective amount of a compound of claim 1, a prodrug of said compound or a pharmaceutically acceptable salt of said compound or prodrug.

30. The method of claim 29 wherein the inflammatory disease is selected from the group consisting of arthritis, asthma, rhinitis and immunomodulation.

* * * * *